(12) United States Patent
Matsuura

(10) Patent No.: US 11,224,391 B2
(45) Date of Patent: Jan. 18, 2022

(54) RADIOGRAPHY APPARATUS

(71) Applicant: FUJIFILM Corporation, Tokyo (JP)

(72) Inventor: Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/858,305

(22) Filed: Apr. 24, 2020

(65) Prior Publication Data

US 2020/0337656 A1  Oct. 29, 2020

(30) Foreign Application Priority Data

Apr. 26, 2019 (JP) .............................. JP2019-085529

(51) Int. Cl.
*H05G 1/06* (2006.01)
*H05G 1/02* (2006.01)
(Continued)

(52) U.S. Cl.
CPC .............. *A61B 6/4441* (2013.01); *A61B 6/42* (2013.01); *A61B 6/54* (2013.01); *G01N 23/046* (2013.01)

(58) Field of Classification Search
CPC .... A61B 6/02; A61B 6/06; A61B 6/12; A61B 6/4007; A61B 6/42; A61B 6/4291; A61B 6/4405; A61B 6/4411; A61B 6/4441; A61B 6/467; A61B 6/487; A61B 6/54; A61B 6/032; A61B 6/463; A61B 6/025; A61B 6/547; A61B 6/469; A61B 5/055; A61B 6/504; A61B 6/5223; A61B 6/542; A61B 6/027; A61B 6/4085; A61B 6/4435; A61B 6/461; A61B 6/466; A61B 6/502; A61B 6/5235; A61B 6/03; A61B 6/035; A61B 6/5241; A61B 6/037; A61B 6/0487; A61B 6/4266; A61B 6/4417; A61B 8/464; A61B 8/465; A61B 8/466; A61B 6/08; A61B 6/14; A61B 6/4476; A61B 6/587; A61B 6/4035; G01N 23/046; G01N 21/4795; G01N 2223/419; G01N 2021/845; G01N 2021/8466; G01N 21/85; G01N 2800/10;
(Continued)

(56) References Cited

U.S. PATENT DOCUMENTS

2010/0246759 A1  9/2010  Ogura et al.
2014/0229883 A1*  8/2014  Tsukijishin .......... A61B 6/4464
715/773
(Continued)

FOREIGN PATENT DOCUMENTS

JP  2010-233962 A  10/2010

*Primary Examiner* — Irakli Kiknadze
(74) *Attorney, Agent, or Firm* — Birch, Stewart, Kolasch & Birch, LLP

(57) ABSTRACT

A radiography apparatus includes a radiation generation unit that has a plurality of radiation sources generating radiation toward a subject, a C-arm that supports the radiation generation unit in a first end portion as one end, a radiography unit that is provided in a second end portion as the other end of the C-arm to face the radiation generation unit and images the subject using radiation, an imaging direction designation unit that designates an imaging direction of the subject, and a radiation source selection unit that selects the radiation source for use in imaging among the plurality of radiation sources using the designation of the imaging direction.

22 Claims, 14 Drawing Sheets

(51) Int. Cl.
*G01N 23/04* (2018.01)
*A61B 6/00* (2006.01)
*G01N 23/046* (2018.01)

(58) Field of Classification Search
CPC ....... G01N 2800/105; G01N 2223/612; G21K 1/04; G21K 1/02; G21K 1/025; G01T 1/2985; G01T 1/026; G01T 1/1603; G01T 1/1642; G01T 1/1648; A61N 5/1042; G06T 2207/30068; G06T 2207/10016; G06T 2207/10132; G06T 7/0012; G06T 2207/10012; G06T 2207/10116; G06T 7/593; G06T 7/41; H01L 27/1446; H01L 27/14603; H01L 27/14658; H01L 27/14812; H05G 1/28; H05G 1/38; H05G 1/42; H01J 35/1017
USPC ............................................ 378/62, 193–198
See application file for complete search history.

(56) References Cited

U.S. PATENT DOCUMENTS

| | | | |
|---|---|---|---|
| 2016/0055639 A1* | 2/2016 | Hara .................... | A61B 6/5247 |
| | | | 345/419 |
| 2018/0184992 A1* | 7/2018 | Li ......................... | A61B 6/037 |

* cited by examiner

RADIOGRAPHY APPARATUS

CROSS-REFERENCE TO RELATED APPLICATIONS

This application claims priority under 35 U.S.C § 119(a) to Japanese Patent Application No. 2019-085529 filed on 26 Apr. 2019. The above application is hereby expressly incorporated by reference, in its entirety, into the present application.

BACKGROUND OF THE INVENTION

1. Field of the Invention

The present invention relates to a radiography apparatus.

2. Description of the Related Art

There are some radiography apparatuses including a radiation source that generates radiation and a radiography unit that images a subject using the radiation. In such radiography apparatuses, the radiation source and the radiography unit are supported by one arm, and a relative positional relationship between the radiation source and the radiography unit is defined. For example, an X-ray imaging apparatus in which an X-ray source and an X-ray imaging panel are supported with a C-arm is known.

In recent years, a radiography apparatus that irradiates a subject with a plurality of radiation rays generated using a plurality of electron sources arranged in one-dimensional or two-dimensional manner is known (JP2009-087836A). The radiography apparatus described in JP2009-087836A captures a plurality of first radiographic images based on detection of a plurality of radiation rays at different irradiation angles irradiating the subject from a plurality of transmissive targets and specifies an object region based on a plurality of first radiographic images, thereby deciding the electron source to be driven from among a plurality of electron sources based on the specified object region. Then, a radiation dose in capturing a second radiographic image is set to be smaller than a radiation source in capturing the first radiographic image using the decided electron source.

SUMMARY OF THE INVENTION

In a case where the radiation source and the radiography unit are supported by one arm, since the relative positions of the radiation source and the radiography unit are fixed, there is an advantage that the alignment of the radiation source and the radiography unit is not needed, or the like.

However, in the radiography apparatus in which the radiation source and the radiography unit are supported by one arm, in a case where the subject is imaged from a direction other than a specific direction aligned with the arm, there is the inconvenience that the position adjustment of the radiation source and the radiography unit should be performed again together with the arm. For example, in a case where an artificial object, such as a bolt, is inserted into a human body as a subject, there is a need to perform imaging from a plurality of directions in conformity with the axis of the bolt or the like in order to confirm whether or not the bolt or the like is correctly inserted. In this case, there is a need to move or incline the arm each time the direction of imaging is changed.

An object of the invention is to provide a radiography apparatus capable of simply imaging a subject from a plurality of directions in a case where a radiation source and a radiography unit are supported by a support member, such as an arm.

A radiography apparatus of the invention comprises a radiation generation unit that has a plurality of radiation sources generating radiation toward a subject, a support member that supports the radiation generation unit in a first end portion as one end of the support member, a radiography unit that is provided to face the radiation generation unit in a second end portion as the other end of the support member and images the subject using the radiation, an imaging direction designation unit that designates an imaging direction of the subject, and a radiation source selection unit that selects the radiation source for use in imaging among the plurality of radiation sources using the designation of the imaging direction.

It is preferable that the imaging direction designation unit designates the imaging direction based on an input from an operating unit provided in the radiation generation unit, the support member, or the radiography unit.

It is preferable that the operating unit is provided in the radiation generation unit or the first end portion of the support member.

It is preferable that the operating unit is provided in the radiography unit or the second end portion of the support member.

It is preferable that the imaging direction designation unit is connected to a first operating unit provided in the radiation generation unit or the first end portion of the support member and a second operating unit provided in the radiography unit or the second end portion of the support member, and the first operating unit is validated in a case where the radiation generation unit is on a vertical upward direction side with respect to the radiography unit, and the second operating unit is validated in a case where the radiation generation unit is on a vertical downward direction side with respect to the radiography unit.

It is preferable that the operating unit displays the imaging direction.

It is preferable that the operating unit receives an input of the imaging direction.

It is preferable that the operating unit receives the input of the imaging direction indirectly by receiving the selection of the radiation source for use in imaging among the plurality of radiation sources.

It is preferable that the operating unit receives the input of the imaging direction through a touch of an operator.

It is preferable that the operating unit receives the input of the imaging direction through motion or voice of an operator.

It is preferable that the imaging direction designation unit designates the imaging direction using a radiographic image.

It is preferable that the radiography apparatus further comprises a display unit that displays the radiographic image, and an input of the imaging direction is received in the radiographic image displayed on the display unit.

It is preferable that selection of two or more points in the radiographic image is received, and the imaging direction designation unit designates the imaging direction based on positions of the selected two or more points.

It is preferable that the imaging direction designation unit designates the imaging direction parallel to or perpendicular to a three-dimensional straight line passing through the selected two or more points.

It is preferable that selection of a structure included in the subject in the radiographic image is received, and the imaging direction designation unit designates the imaging direction based on a position or a shape of the selected structure.

It is preferable that the imaging direction designation unit designates a direction parallel to a longitudinal direction of the structure or a direction perpendicular to the longitudinal direction of the structure as the imaging direction.

It is preferable that, in a case where a tomographic image is acquired, at least one of selection of a slice direction as a direction of forming the tomographic image with respect to the subject in the radiographic image or selection of a slice position as a position for forming the tomographic image with respect to the subject in the radiographic image is received.

It is preferable that selection of two or more points in the radiographic image is received, at least one of the slice direction or the slice position is changed based on positions of the selected two or more points, and the imaging direction designation unit designates the imaging direction based on the positions of the selected two or more points.

It is preferable that selection of a structure included in the subject in the radiographic image is received, at least one of the slice direction or the slice position is changed based on a position or a shape of the selected structure, and the imaging direction designation unit designates the imaging direction based on the position or the shape of the selected structure.

It is preferable that tomographic video composed of the tomographic image is acquired by continuously or intermittently acquiring the tomographic image by imaging the subject.

It is preferable that, in a case where fluoroscopy is performed on the subject, the tomographic image is automatically acquired through imaging after fluoroscopy ends.

It is preferable that the radiography apparatus further comprises a notification unit that prompts movement of the support member in a case where the radiation source selection unit is unable to select the radiation source using the imaging direction designated by the imaging direction designation unit.

It is preferable that the notification unit gives notification of at least one of a direction of movement or an amount of movement of the support member.

According to the invention, it is possible to provide a radiography apparatus capable of simply imaging a subject from a plurality of directions in a case where a radiation source and a radiography unit are supported by a support member, such as an arm.

DESCRIPTION OF THE PREFERRED EMBODIMENTS

First Embodiment

Figure 1:
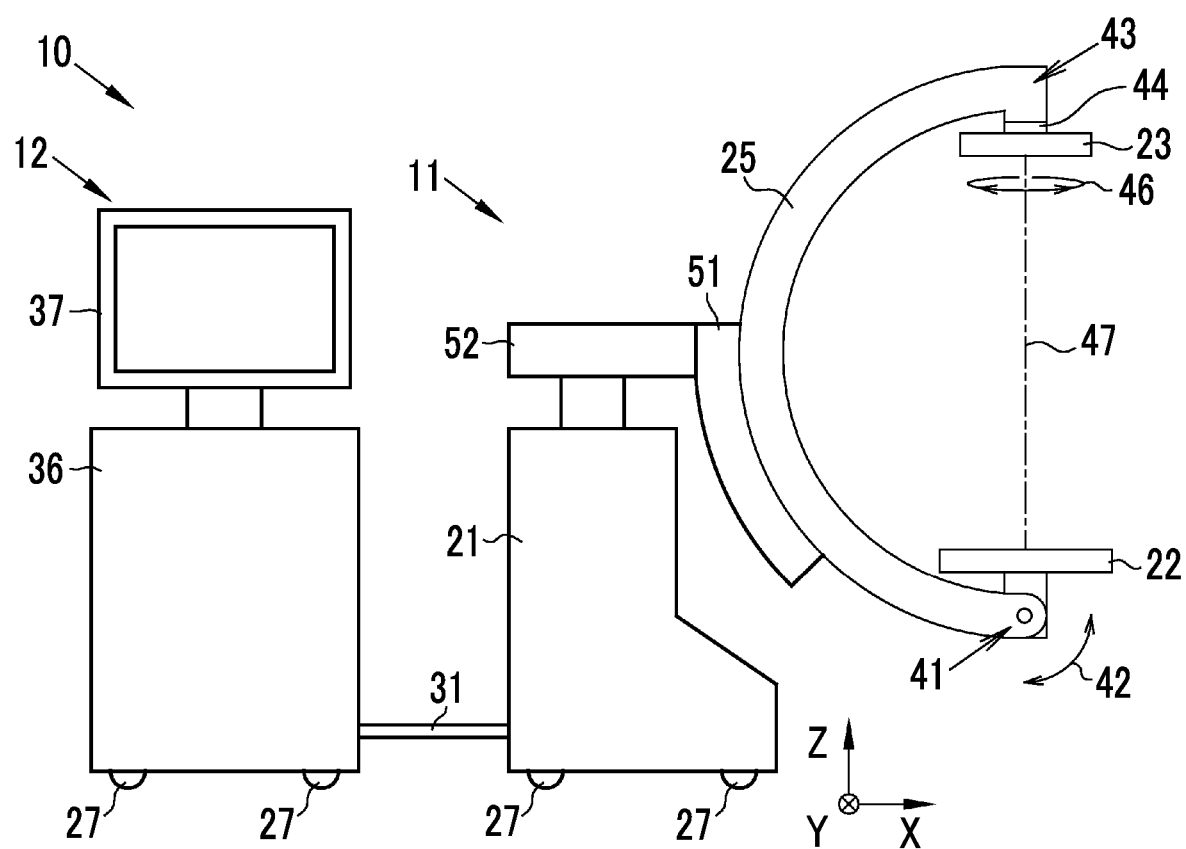
FIG. 1 is a schematic view of a radiography apparatus.

As shown in FIG. 1, a radiography apparatus 10 comprises an imaging unit 11, a display unit 12, and a console (not shown). The imaging unit 11 is a unit that generates radiation and images a subject 15 (see FIG. 4) using radiation. The display unit 12 is a unit that displays or the like a radiographic image captured using the imaging unit 11. The console is an integral control console of the radiography apparatus 10, and is a so-called computer. The console is a unit that acquires, inputs, or the like an imaging menu based on setting, a request, or the like. The imaging unit 11 and the display unit 12 are disposed in an imaging room, an operating room, or the like. The console is disposed, for example, in a room different from the imaging room, the operating room, or the like. While the console can be disposed in the imaging room or the operating room, in this case, the console is disposed at a position apart from the imaging unit 11 and the display unit 12. This is to restrain obstruction to the operation of at least one of the imaging unit 11 or the display unit 12.

The imaging unit 11 comprises an imaging unit body 21, a radiation generation unit 22, a radiography unit 23, and a C-arm 25.

The imaging unit body 21 integrally controls the operation of the radiation generation unit 22, the radiography unit 23, the C-arm 25, and the like. The imaging unit body 21 is connected to the display unit 12 in a wired or wireless manner. In the embodiment, the imaging unit body 21 is connected to the display unit 12 using a cable 31 in a wired manner. With this, the imaging unit 11 suitably transmits or receives a radiographic image, information related to imaging of the radiographic image, and the like to or from the display unit 12. The display unit 12 comprises a display unit body 36, and a monitor 37 that displays a radiographic image and the like. Casters 27 are attached to the imaging unit body 21 and the display unit body 36. For this reason, the radiography apparatus 10 is movable, and can carry out radiography, for example, in a patient's room where a patient as the subject 15 is present.

The radiation generation unit 22 generates radiation toward the subject 15 disposed between the radiation generation unit 22 and the radiography unit 23 in a case where radiography is performed. The radiation generation unit 22 is rotationally movably attached to a first end portion 41 as one end of the C-arm 25. In the embodiment, the rotational movement of the radiation generation unit 22 can be made within the plane of the C-arm 25. For example, in a case where the C-arm 25 is disposed within an XZ plane (see FIG. 1), the radiation generation unit 22 can rotationally move in an XZ in-plane direction as indicated by an arrow 42. In the embodiment, although radiation generated in the radiation generation unit 22 is X-rays, the radiation generation unit 22 can be substituted with a configuration in which radiation other than X-rays is generated.

The radiography unit 23 is attached to a second end portion 43 as the other end (an end portion opposite to the end portion to which the radiation generation unit 22 is attached) of the C-arm 25 in an attachable and detachable manner and a rotatable manner to face the radiation generation unit 22. A state in which the radiography unit 23 "faces the radiation generation unit 22" refers to a state in which the radiography unit 23 is disposed in a position and a direction in which radiation generated by the radiation generation unit 22 can be received through the subject 15. The radiography unit 23 images the subject 15 using the radiation generated by the radiation generation unit 22. The detection unit 44 is a mechanism that detects a attachment and detachment state and a rotation state of the radiography unit 23, and includes, for example, a switch mechanism that is turned on in a case where the radiography unit 23 is attached, a sensor that detects a direction in which the radiography unit 23 is mounted, and the like. In the embodiment, the detection unit 44 is embedded in the second end portion 43 in which the C-arm 25 is attached to the radiography unit 23. The attachment and detachment of the radiography unit 23 includes attachment and detachment of a part of components of the radiography unit 23. The radiography unit 23 is rotatable right and left (or forward and backward) around a center line 47 connecting the first end portion 41 and the second end portion 43 as indicated by an arrow 46. The radiography unit 23 can rotate upon or after the attachment to the second end portion 43. The detection unit 44 can detect a size (so-called panel size) of an effective detection region of the radiography unit 23 in addition to the attachment and detachment and the rotation of the radiography unit 23. For this reason, the detection unit 44 can acquire information related to an ID, a model, or the like of the radiography unit 23, for example, directly from the radiography unit 23.

The C-arm 25 is a support member that supports the radiation generation unit 22 in the first end portion 41 as one end and supports the radiography unit 23 in the second end portion 43 as the other end. In the embodiment, in a case where both of the radiation generation unit 22 and the radiography unit 23 are attached to the C-arm 25, the C-arm 25 is held at a position (hereinafter, referred to as a confronting position) where the radiation generation unit 22 and the radiography unit 23 are in a confronting state. The confronting position refers to an arrangement in which a normal passing through the center (a center C1 (see FIG. 11) of a surface where radiation is generated) of the radiation generation unit 22 coincides with a normal passing through the center (a center C2 (see FIG. 11) of a surface where effective pixels are present) of the radiography unit 23. In the embodiment, the center line 47 connecting the first end portion 41 and the second end portion 43 is the normal passing through the center of the radiation generation unit 22, and is the normal passing through the center of the radiography unit 23. The radiography apparatus 10 can detach the radiography unit 23 from the C-arm 25 to perform radiography. In this case, the C-arm 25 can hold the radiation generation unit 22 in arbitrary position and direction. For example, the C-arm 25 can dispose the radiation generation unit 22 in a position and a direction confronting the radiography unit 23 detached from the second end portion 43.

Figure 2:
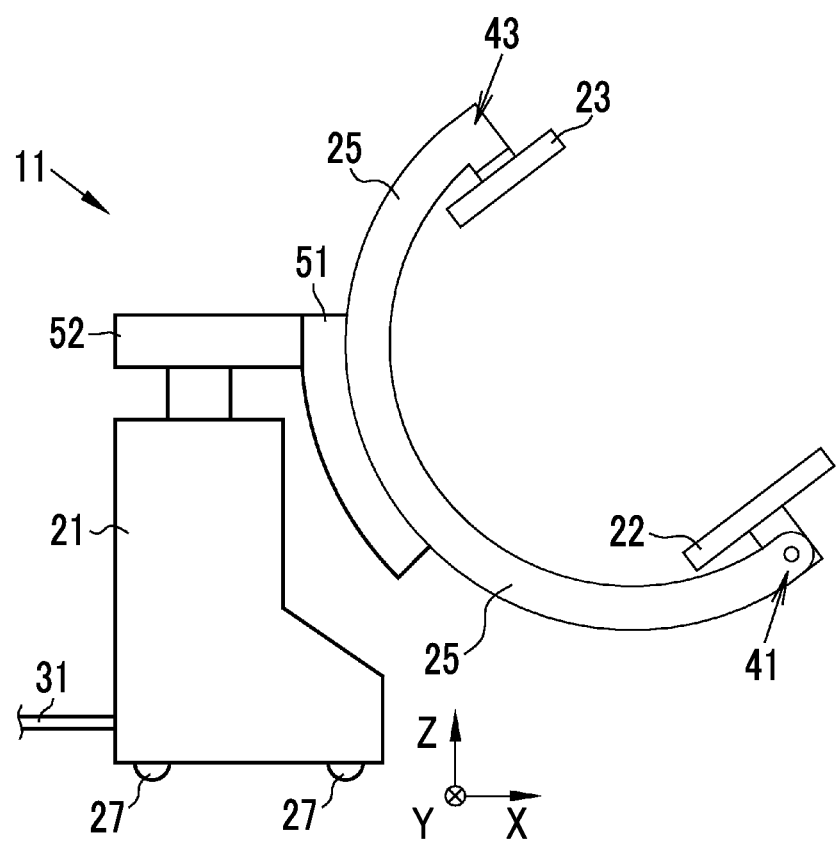
FIG. 2 shows the radiography apparatus in which a C-arm is slid.

The C-arm 25 is connected to a lifting mechanism 52 through a sliding mechanism 51. The sliding mechanism 51 slidably holds the C-arm 25 in an arc shape. As the C-arm 25 is slid by the sliding mechanism 51, the radiation generation unit 22 and the radiography unit 23 can be rotated around the center (the center of a "C" shape that is an arc) of the C-arm 25 while maintaining a relative positional relationship. For example, in a case where the radiation generation unit 22 and the radiography unit 23 are disposed within the XZ plane as shown in FIG. 1, as shown in FIG. 2, as the C-arm 25 is slid using the sliding mechanism 51, the C-arm 25 and the radiation generation unit 22 and the radiography unit 23 attached to the C-arm 25 can be rotated around a Y axis. In FIG. 2, as the C-arm 25 is slid in a positive direction around the Y axis, the radiography unit 23 is moved in a direction of approaching the imaging unit body 21 and the radiation generation unit 22 is moved in a direction of being away from the imaging unit body 21; however, as the C-arm 25 is slid in a negative direction around the Y axis, the radiography unit 23 can be moved in a direction away from the imaging unit body 21 and the radiation generation unit 22 can be moved in a direction of approaching the imaging unit body 21. The same applies to a slide other than the slide around the Y axis.

Figure 3:
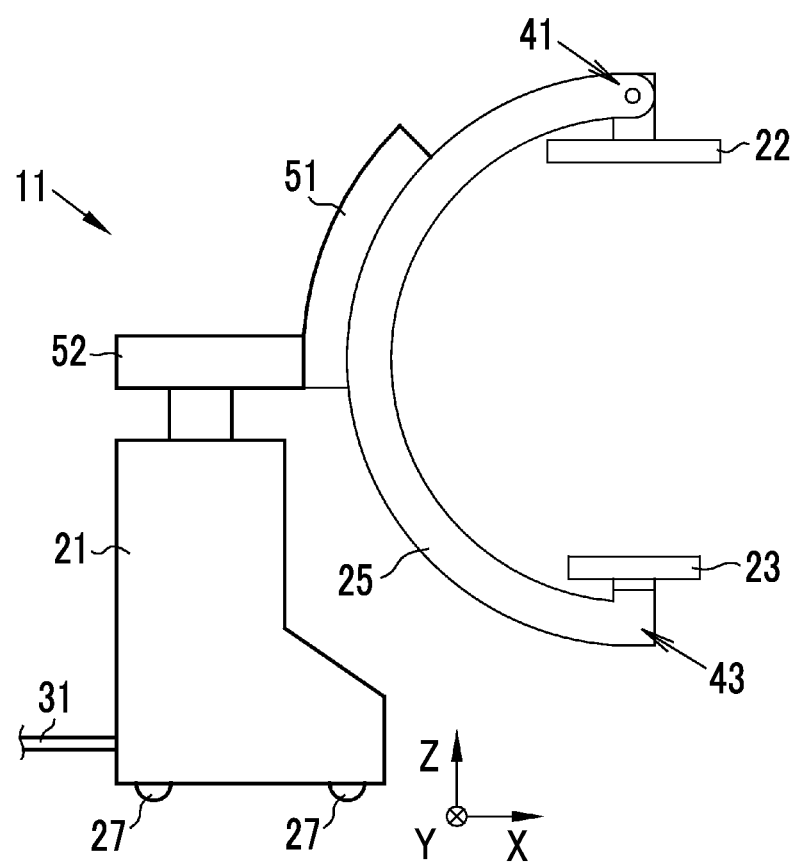
FIG. 3 shows the radiography apparatus in which the C-arm is rotated.

The sliding mechanism 51 is rotatably attached to the lifting mechanism 52 attached to the imaging unit body 21 liftably in a vertical direction (Z-axis direction). For example, as shown in FIG. 3, the C-arm 25 can be freely rotated around a specific direction (X-axis) within a horizontal plane. As the lifting mechanism 52 is lifted up and down, the C-arm 25 and the radiation generation unit 22 and the radiography unit 23 attached to the C-arm 25 can be moved arbitrarily in a vertical upward direction (Z-axis positive direction) or a vertical downward direction (Z-axis negative direction).

Figure 4:
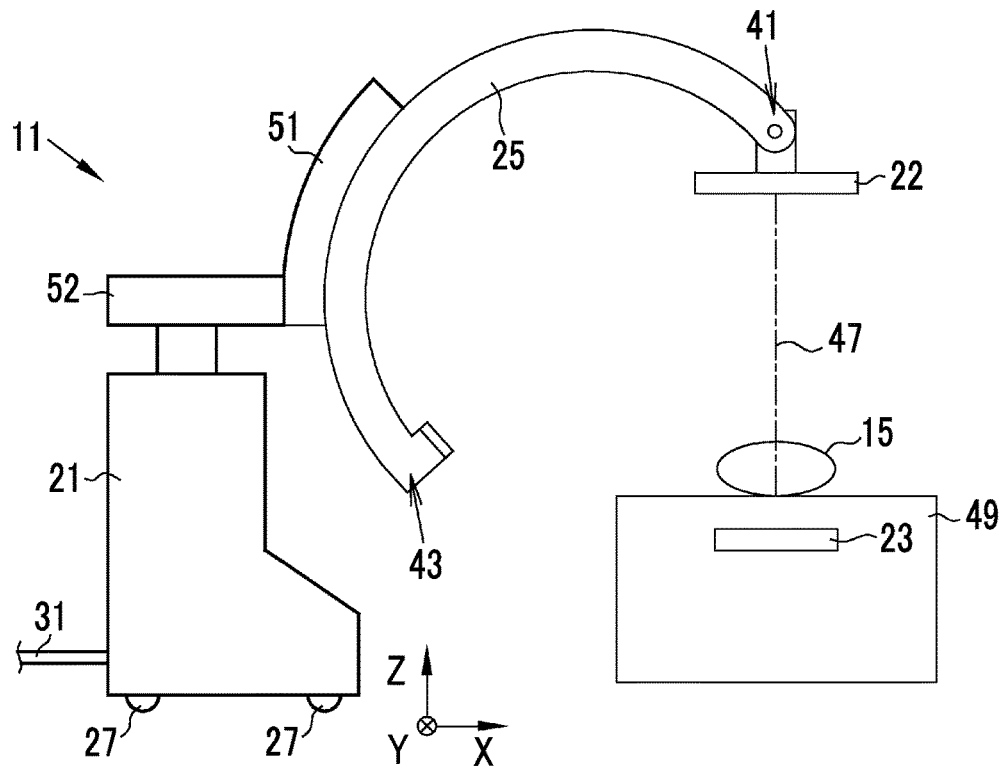
FIG. 4 is a schematic view of a case where a radiography panel is separated to perform imaging.

In addition, in a case where the radiography unit 23 is detached from the second end portion 43, and the radiography unit 23 is disposed on a bed 49 on which the subject 15 lies, as shown in FIG. 4, the radiation generation unit 22 can be disposed at a confronting position with respect to the radiography unit 23 by combining the slide and rotation of the C-arm 25 and the rotation of the radiation generation unit 22 with respect to the first end portion 41.

The radiography apparatus 10 configured as above can image the subject 15 in a form of a static image or video using radiation. In the embodiment, the radiography apparatus 10 can perform a plurality of kinds of radiography, such as general imaging (simple imaging), fluoroscopy, tomography, and tomographic video imaging. General imaging is an imaging form (so-called X-raying) in which one or a plurality of radiographic images (static image) are obtained. Fluoroscopy is an imaging form in which video composed of a plurality of radiographic images is obtained by continuously or intermittently imaging the subject using radiation. Tomography is an imaging form in which a tomographic image (so-called tomosynthesis image) representing an arbitrary cross section of the subject is obtained by imaging the subject from a plurality of different directions and recomposing a plurality of obtained radiographic images. Tomographic video imaging is an imaging form in which video of a tomographic image is obtained by continuously or intermittently obtaining one or a plurality of specific tomographic images. Each imaging form can be carried out arbitrarily without depending on the direction or the like of the C-arm 25.

Figure 5:
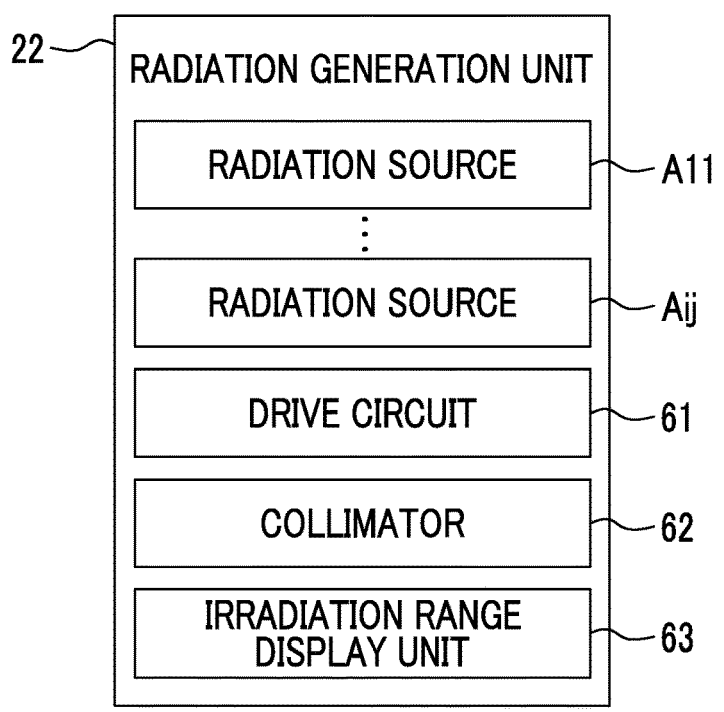
FIG. 5 is a block diagram of a radiation generation unit.

As shown in FIG. 5, the radiation generation unit 22 comprises a plurality of radiation sources A11 to Aij (where "i" and "j" are positive integers), a drive circuit 61, a collimator 62, and an irradiation range display unit 63.

Figure 6:
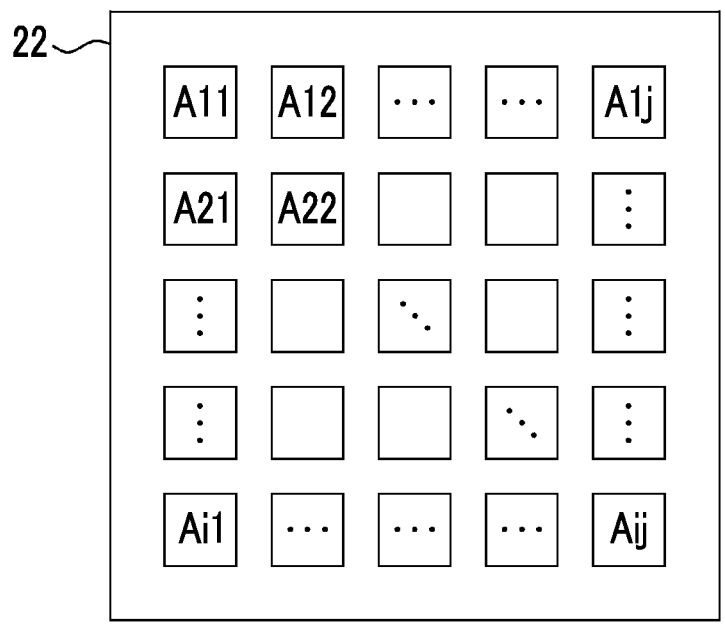
FIG. 6 is an explanatory view showing an example of an arrangement of a plurality of radiation sources in the radiation generation unit.

A plurality of radiation sources A11 to Aij are arranged, for example, in a one-dimensional or two-dimensional manner to face the radiography unit 23. In the embodiment, as shown in FIG. 6, a plurality of radiation sources A11 to Aij are arranged in a two-dimensional manner of "i" rows and "j" columns. A plurality of radiation sources A11 to Aij can be driven individually, and generate radiation. A plurality of radiation sources A11 to Aij are arbitrary combined, and a plurality of kinds of radiation sources that are different in quality of radiation or the like can be used. In the embodiment, all of a plurality of radiation sources A11 to Aij are X-ray sources (X-ray tubes). The radiation sources A11 to Aij have the same quality and generate X-rays having substantially the same quality of radiation in a case where conditions related to driving, such as a tube voltage and a tube current, are the same.

As described above, the radiation generation unit 22 has a plurality of radiation sources. For this reason, in a case where radiography is performed, the radiation generation unit 22 can generate radiation substantially simultaneously using one or a plurality of radiation sources or all of the radiation sources among a plurality of radiation sources A11 to Aij as needed. In the embodiment, it is assumed that the radiation generation unit 22 generates radiation from one radiation source among a plurality of radiation sources A11 to Aij. This is to maintain the sharpness of a radiographic image. For example, in a case where general imaging and fluoroscopy are performed, the radiation generation unit 22 generates radiation selectively using one radiation source among a plurality of radiation sources A11 to Aij. In a case where tomography and tomographic video imaging are performed, imaging is performed multiple times in order to obtain one tomographic image; however, in each imaging, the radiation generation unit 22 selectively uses one radiation source among a plurality of radiation sources A11 to Aij. The radiation generation unit 22 transitions the radiation source for use in generating radiation in each imaging, for example, in an order of the radiation source A11, the radiation source A22, . . . , and the radiation source Aij. In this way, the radiography apparatus 10 changes a direction (hereinafter, referred to as an imaging direction), in which radiography is performed on the subject 15, by selecting the radiation source for use in generating radiation from among a plurality of radiation sources A11 to Aij.

The drive circuit 61 is a drive circuit that drives a plurality of radiation sources A11 to Aij, and is a so-called high voltage generation circuit. The drive circuit 61 supplies electric power needed for generating radiation to one or a plurality of radiation sources among a plurality of radiation sources A11 to Aij. The drive circuit 61 can be constituted of an aggregate of circuits respectively provided in the radiation sources A11 to Aij, one or a plurality of circuits capable of switching a supply destination of electric power among the radiation sources A11 to Aij, or the like. A high voltage in the drive circuit 61 refers to a voltage needed for each of the radiation sources A11 to Aij to generate radiation. For the radiation generation unit 22, a so-called monotank in which the radiation sources A11 to Aij and the drive circuit 61 are integrated can be used.

Figure 7:
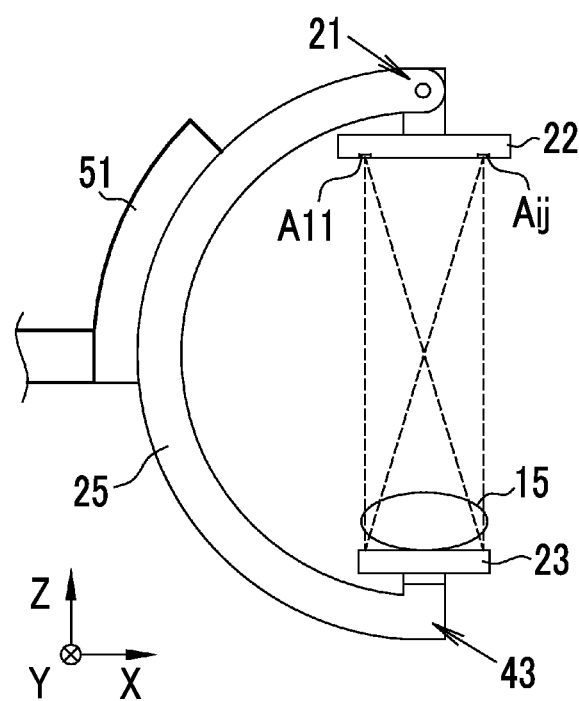
FIG. 7 is an explanatory view showing an irradiation range of radiation generated by each radiation source.

The collimator 62 is a mechanism that adjusts an irradiation range of radiation. In the embodiment, the collimator 62 individually adjusts the irradiation range of radiation generated by each of the radiation sources A11 to Aij. For example, as shown in FIG. 7, the collimator 62 adjusts the irradiation range of radiation generated by each of the radiation sources A11 to Aij to a region where effective pixels of the radiography unit 23 are present and a surrounding region. With this, it is possible to reduce the exposure of the subject 15. The collimator 62 can be provided for all of the radiation sources A11 to Aij. In this case, it is possible to adjust the irradiation range of radiation to a specific range as the whole of the radiation generation unit 22 without depending on which radiation source among a plurality of radiation sources A11 to Aij is used. In this case, it is also possible to reduce the exposure of the subject 15 compared to a case where the irradiation range of radiation is not adjusted.

The irradiation range display unit 63 is a light-emitting element, such as a light-emitting diode or a lamp, and irradiates the subject 15 with visible light mostly from near a generation point (so-called focal point) of X-rays through the collimator 62. With this, the irradiation range display unit 63 displays the irradiation range of radiation adjusted by the collimator 62 on the subject 15 using visible light.

Figure 8:
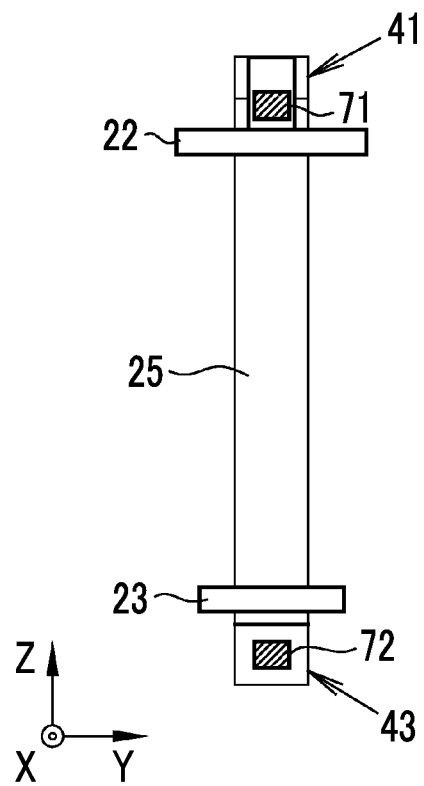
FIG. 8 is an explanatory view showing a first operating unit and a second operating unit.

In addition to the above, as shown in FIG. 8, the radiography apparatus 10 comprises a first operating unit 71 in the first end portion 41 of the C-arm 25, and comprises a second operating unit 72 in the second end portion 43 of the C-arm 25. The first operating unit 71 and the second operating unit 72 are operating units that are used in a case where an operator of the radiography apparatus 10 (hereinafter, referred to as an operator), such as a physician or a radiological technician, inputs various kinds of information related to imaging, such as an imaging direction or imaging conditions, from the imaging unit 11. The first operating unit 71 and the second operating unit 72 can include a display unit that displays information needed for an operation. The first operating unit 71 and the second operating unit 72 include, for example, buttons that are used to input an imaging direction or the like, and a display unit that displays a selected (or selectable) imaging direction or the like. In this case, for the first operating unit 71 and the second operating unit 72, for example, a touch panel can be used. The display unit in each of the first operating unit 71 and the second operating unit 72 can display at least one of a radiographic image or an image obtained by imaging the subject 15 with visible light (for infrared light) or the like as needed.

Figure 9:
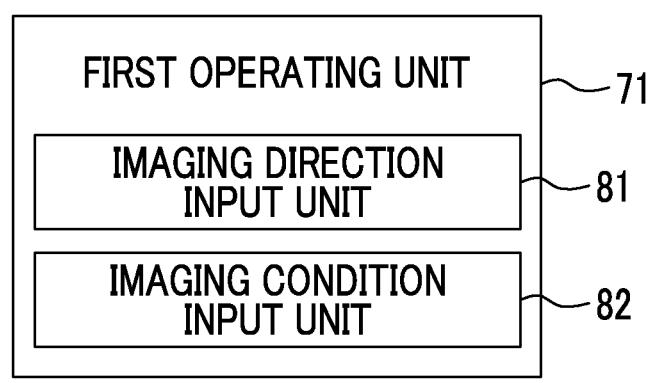
FIG. 9 is a block diagram of the first operating unit.
Figure 10:
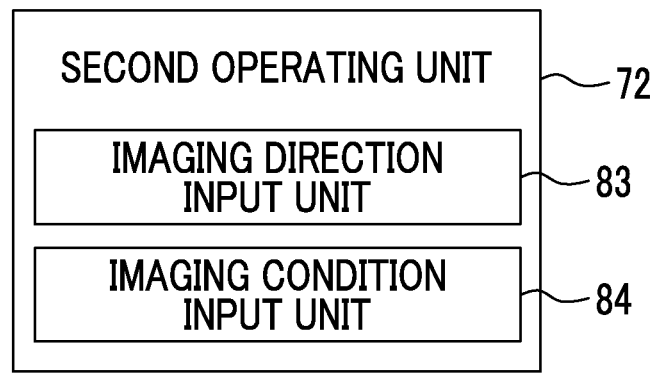
FIG. 10 is a block diagram of the second operating unit.

For example, as shown in FIG. 9, the first operating unit 71 comprises an imaging direction input unit 81 and an imaging condition input unit 82. The imaging direction input unit 81 receives an input of setting (selection) or change of the imaging direction. The imaging condition input unit 82 receives an input of setting (selection) or change of the imaging conditions. Similarly, as shown in FIG. 10, the second operating unit 72 comprises an imaging direction input unit 83 and an imaging condition input unit 84. The imaging direction input unit 83 receives an input of setting (selection) or change of the imaging direction. The imaging condition input unit 84 receives an input of setting (selection) or change of the imaging conditions.

Figure 11:
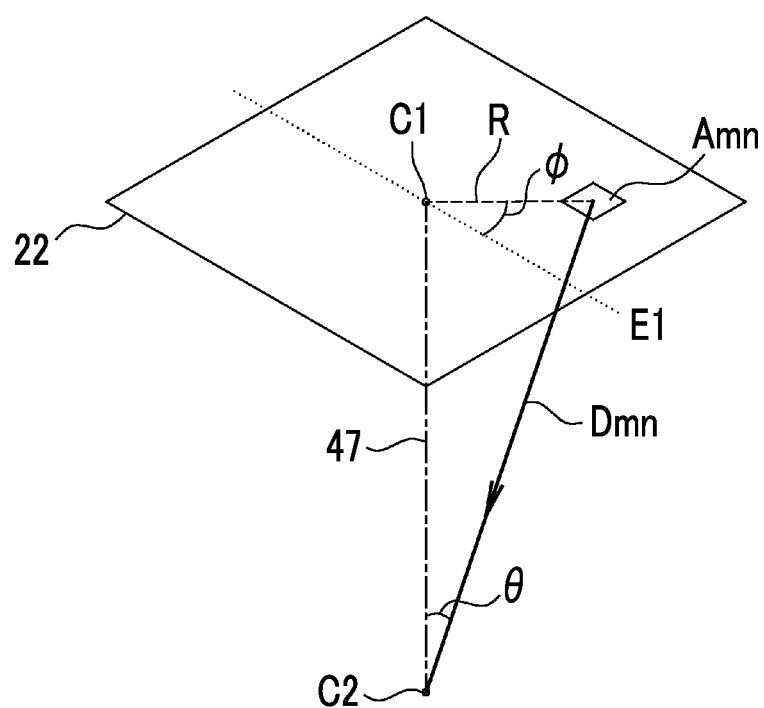
FIG. 11 is an explanatory view showing an imaging direction and a position of a radiation source.

The "imaging direction" is a direction in which radiography is performed on the subject 15, that is, a direction in which the subject 15 is irradiated with radiation. Then, the "imaging direction" is information with which a position of a radiation source for use in imaging can be decided. For example, as shown in FIG. 11, in a case where the radiation generation unit 22 and the radiography unit 23 are disposed at the confronting position on the center line 47 connecting the first end portion 41 and the second end portion 43, the distance (so-called source-image distance (SID); in FIG. 11, C1-C2 distance) between the radiation generation unit 22 and the radiography unit 23 is known by the C-arm 25. For this reason, in a case where an imaging direction Dmn is determined, an angle θ between the imaging direction Dmn and the center line 47, an angle φ measured based on an arbitrary axis E1 from the center C1 in the radiation generation unit 22, a distance "R" from the center C1 in the radiation generation unit 22, and the like are automatically determined. For this reason, in a case where the imaging direction Dmn is determined, the radiation generation unit 22 can specify a position of a radiation source Amn (one radiation source among the radiation sources A11 to Aij) to be used in imaging.

The "imaging conditions" are conditions related to radiography, and are, for example, a tube voltage and a radiation dose (a tube current and an exposure time) of each of the radiation sources A11 to Aij, use or non-use of a grid, an aspect ratio of the grid, use or non-use of a gel pad, and the like.

The first operating unit 71 and the second operating unit 72 are, for example, devices that receive an input of the imaging direction through a touch of the operator (including a press of a mechanical or electrical button). In particular, in the embodiment, the first operating unit 71 and the second operating unit 72 are touch panels. Then, the imaging direction input unit 81 and the imaging condition input unit 82 in the first operating unit 71 and the imaging direction input unit 83 and the imaging condition input unit 84 in the second operating unit 72 are a so-called graphical user interface (GUI).

However, the first operating unit 71 and the second operating unit 72 can receive the input of the imaging direction or the like by voice, a gesture, or the like instead of using the GUI or in parallel with the use of the GUI without needing a touch of the operator. In a case where an input through voice of the operator is received, the first operating unit 71 and the second operating unit 72 include a microphone that picks up voice (sound generated using a vocal cord or sound generated using another part or an object) from the operator, and an analysis unit that analyzes the picked-up voice to acquire the content of an operation input including the voice. In a case where an input through a gesture (for example, at least one of a body gesture, a hand gesture, or the like) of the operator is received, the first operating unit 71 and the second operating unit 72 include an imaging unit (so-called camera, a video camera, or the like) that images the operator, and an analysis unit that analyzes an image or video of the operator captured by the imaging unit to acquire the content of an operation input represented by motion of the operator. The gesture of the operator includes changes in partial shape or the like of the body, such as movement of a line of sight, a locus of movement of the line of sight, a blinking speed, and the number of blinks, in addition to the body gesture (body motion) or a hand gesture (hand motion) of the operator. In a case where the first operating unit 71 and the second operating unit 72 are configured to receive an input through voice, a gesture, or the like, even though the operator is at a position hard to come into contact with the first operating unit 71 or the second operating unit 72, the operator can perform the input of the imaging direction or the like. Thus, usability is improved compared to a case where an input through voice, a gesture, or the like is not received.

Figure 12:
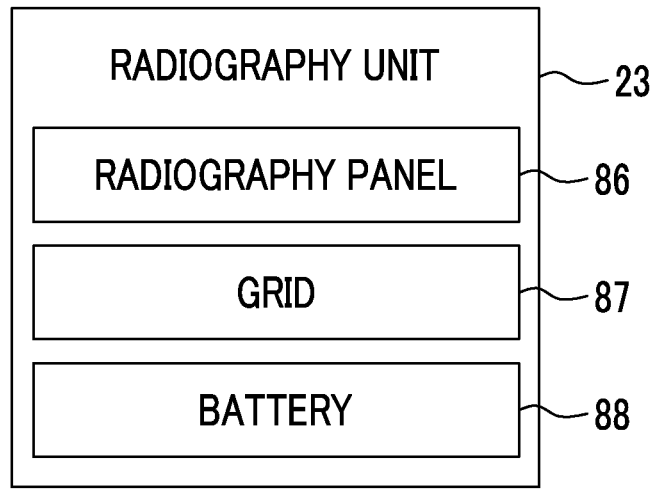
FIG. 12 is a block diagram of a radiography unit.

As shown in FIG. 12, the radiography unit 23 comprises a radiography panel 86, a grid 87, a battery 88, and the like.

The radiography panel 86 receives radiation generated by the radiation generation unit 22 to image the subject 15. For example, the radiography panel 86 (or the entire radiography unit 23) is a so-called direct conversion type or indirect conversion type flat panel detector (FPD). In the embodiment, the radiography panel 86 in the radiography unit 23 can be replaced with another radiography panel that is different in panel size or the like.

The grid 87 is a member that improves the resolution or the like of a radiographic image by eliminating scattered radiation, and is disposed on an incidence side of radiation of the radiography panel 86 (a side on which the radiation generation unit 22 is present). The grid 87 is attachable and detachable and is used as needed. For example, while the grid 87 is used in general imaging, the grid 87 is not used in fluoroscopy. Even in the imaging form using the grid 87, the grid 87 can be arbitrarily replaced with a grid that is different in aspect ratio or the like. The replacement of the grid 87 can be performed along with the radiography panel 86 or separately from the radiography panel 86. The grid 87 can be included in the radiography panel 86.

The battery 88 is a power supply that supplies electric power to the radiography panel 86. The battery 88 can be included in the radiography panel 86. In the embodiment, since the radiography unit 23 is usable in a state of being detached from the C-arm 25, the battery 88 is mounted in the radiography unit 23; however, in the radiography apparatus 10; however, a radiography panel that is attached to the C-arm 25 and receives the supply of electric power from the imaging unit body 21 to perform radiography can also be used. In this case, the radiography unit 23 can omit the battery 88.

Figure 13:
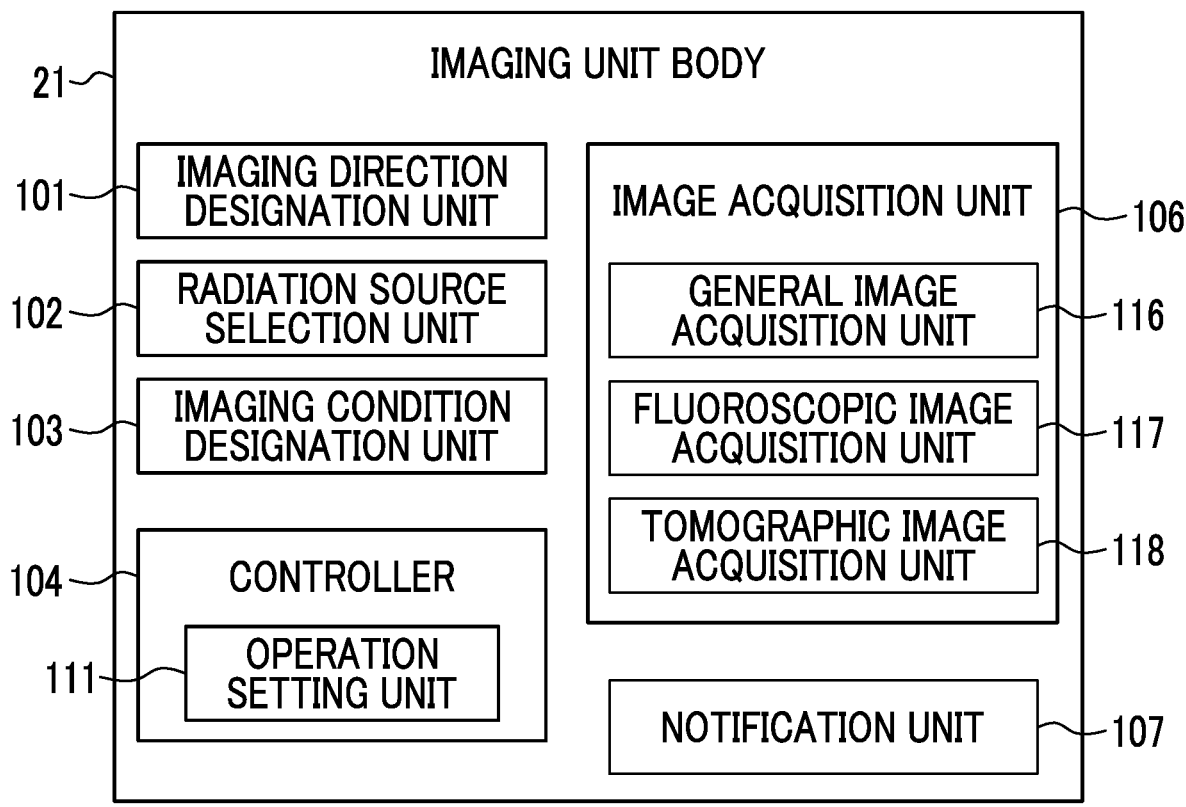
FIG. 13 is a block diagram of an imaging unit body.

As shown in FIG. 13, the imaging unit body 21 comprises an imaging direction designation unit 101, a radiation source selection unit 102, an imaging condition designation unit 103, a controller 104, an image acquisition unit 106, and a notification unit 107.

The imaging direction designation unit 101 designates an imaging direction of the subject directly or indirectly based on an operation input of the operator or an analysis result of a radiographic image or the like. In the embodiment, since the operator designates the imaging direction directly using the imaging direction input unit 81 of the first operating unit 71 or the imaging direction input unit 83 of the second operating unit 72, the imaging direction designation unit 101 designates the imaging direction, for example, by obtaining at least two of the angle θ, the angle φ, and the distance "R" (see FIG. 11) based on the input of the imaging direction input unit 81 of the first operating unit 71 or the imaging direction input unit 83 of the second operating unit 72. Hereinafter, the imaging direction designation unit 101 obtains the angle θ and the angle φ and designates the imaging direction using the angle θ and the angle φ.

The radiation source selection unit 102 selects a radiation source for use in imaging among a plurality of radiation sources A11 to Aij using the designation of the imaging direction in the imaging direction designation unit 101. In a case where there is no radiation source at a position determined by the designation of the imaging direction, the radiation source selection unit 102 selects one radiation source closest to the position determined by the designation of the imaging direction as the radiation source for use in imaging.

In the embodiment, the radiation source selection unit 102 obtains information of the angle θ and the angle φ for the imaging direction input from the imaging direction designation unit 101 by the operator. Then, in a case where there is a radiation source at the position determined by the angle θ and the angle φ from a plurality of radiation sources A11 to Aij, the radiation source is selected as the radiation source for use in imaging. On the other hand, in a case where there is no radiation source at the position determined by the angle θ and the angle φ, the radiation source selection unit 102 selects a radiation source closest to the position determined by the angle θ and the angle φ as the radiation source for use in imaging. In a case where there is no radiation source at the position determined by the angle θ and the angle φ, and there are a plurality of radiation sources closest to the position determined by the angle θ and the angle φ, one radiation source among the radiation sources is selected as the radiation source for use in imaging, for example, randomly. This is to maintain the sharpness of a radiographic image.

The imaging condition designation unit 103 designates imaging conditions using an imaging menu registered in advance. In a case where an input of imaging conditions is input from the console, the imaging condition input unit 82 of the first operating unit 71, or the imaging condition input unit 84 of the second operating unit 72, the imaging condition designation unit 103 designates the imaging conditions.

The controller 104 integrally controls the respective units of the imaging unit body 21. For example, the controller 104 receives an input of an imaging instruction and drives the image acquisition unit 106, thereby executing various kinds of imaging. The controller 104 comprises an operation setting unit 111 that performs control for validating one of the first operating unit 71 and the second operating unit 72 and invalidating the other operating unit based on a pose or the like of the C-arm 25. The operation setting unit 111 acquires the pose of the C-arm 25 from a position sensor and a rotation sensor (not shown) attached to the sliding mechanism 51. The operation setting unit 111 takes an attachment and detachment state of the radiography unit 23 acquired from the detection unit 44 into consideration in a case of validating or invalidating the first operating unit 71 and the second operating unit 72.

Specifically, the operation setting unit 111 validates the first operating unit 71 in a case where the radiation generation unit 22 is on a vertical upward direction side with respect to the radiography unit 23, and validates the second operating unit 72 in a case where the radiation generation unit 22 is on a vertical downward direction side with respect to the radiography unit 23. The "validation of the first operating unit 71 or the second operating unit 72 refers to bringing the operating unit into a state in which the input of the imaging direction or the like from the operator is received. The operation setting unit 111 invalidates the second operating unit 72 in a case where the radiation generation unit 22 is on the vertical upward direction side with respect to the radiography unit 23, and invalidates the first operating unit 71 in a case where the radiation generation unit 22 is on the vertical downward direction side with respect to the radiography unit 23. The "invalidation" of the first operating unit 71 or the second operating unit 72 refers to bringing the operating unit into a state in which the input of the imaging direction or the like from the operator is not received. Since the operator normally holds the end portion on a relatively vertical upward direction side between the first end portion 41 and the second end portion 43 of the C-arm 25 to perform the position adjustment of the radiation generation unit 22 and the radiography unit 23, as described above, in a case where the operating unit on the relatively vertical upward direction side between the first operating unit 71 and the second operating unit 72 is validated, operability is excellent. In a case where the operating unit on a relatively vertical downward direction side between the first operating unit 71 and the second operating unit 72 is invalidated, it is possible to restrain erroneous operation due to contact or the like with the bed 49, other objects, or a person.

In a case where the radiation generation unit 22 and the radiography unit 23 are flush with each other in a vertical direction, the operation setting unit 111 validates the operating unit in the end portion relatively far from the imaging unit body 21 between the first operating unit 71 and the second operating unit 72, and invalidates the operating unit in the end portion relatively close to the imaging unit body 21 between the first operating unit 71 and the second operating unit 72. This is because there is a high possibility that the operator holds or the like the end portion at a position relatively far from the imaging unit body 21 to perform the position adjustment of the radiation generation unit 22 and the radiography unit 23. In a case where the radiography unit 23 is not attached to the second end portion 43, the operation setting unit 111 validates the first operating unit 71 and invalidates the second operating unit 72 in the second end portion 43. This is because, in this case, the operator holds or the like the first end portion 41, in which the radiation generation unit 22 is present, to perform the position adjustment of the radiation generation unit 22.

The image acquisition unit 106 performs general radiographic imaging, video imaging composed of radiographic images, tomography, tomographic video imaging, or the like to acquire a general radiographic image or video composed of radiographic images using the radiation generation unit 22 and the radiography unit 23 by receiving selection of an imaging form and the input of the imaging instruction through the controller 104. For example, the image acquisition unit 106 comprises, for example, a general image acquisition unit 116 that performs general imaging to acquire a radiographic image (general image), a fluoroscopic image acquisition unit 117 that performs fluoroscopy to acquire video (fluoroscopic image) composed of radiographic images, and a tomographic image acquisition unit 118 that performs tomography or tomographic video imaging to obtain a tomographic image or tomographic video. The respective units of the image acquisition unit 106 carry out imaging of the respective forms using the radiation source selected by the radiation source selection unit 102 among a plurality of radiation sources A11 to Aij. The respective units of the image acquisition unit 106 carry out imaging of the respective forms according to the imaging conditions designated by the imaging condition designation unit 103. Hereinafter, in a case where a radiographic image is simply described, the radiographic image includes a general image, a fluoroscopic image, a tomographic image, and tomographic video.

The notification unit 107 prompts movement of the C-arm 25 as a support member, that is, movement of the radiation generation unit 22 and the radiography unit 23 in a case where the radiation source selection unit 102 cannot select a radiation source using the imaging direction designated by the imaging direction designation unit 101. A case where the radiation source selection unit 102 cannot select a radiation source refers to a case where an extension line of the imaging direction is outside the radiation generation unit 22 and all of a plurality of radiation sources A11 to Aij are far from the imaging direction, or the like. For example, in the embodiment, since the imaging direction designation unit 101 designates the imaging direction using the angle θ and the angle φ, the radiation source selection unit 102 compares the distance "R" (see FIG. 11), which can be calculated using the angle θ and the angle φ, with a predetermined threshold value Th1. It is assumed that the threshold value Th1 is, for example, a value greater than a distance Rmax to the radiation source (radiation source A11, Aij, or the like) farthest from the center C1 of the radiation generation unit 22. Then, in a case where the distance "R" determined by the designation of the imaging direction is greater than the threshold value Th1, the radiation source selection unit 102 determines that all of a plurality of radiation sources A11 to Aij are far from the distance "R" determined by the designation of the imaging direction, and inputs, to the notification unit 107, information to the effect that a radiation source cannot be selected using the designation of the imaging direction. The notification unit 107 obtains the input information and prompts the movement of the C-arm 25 as a support member. "Information to the effect that a radiation source cannot be selected" can include information indicating a discrepancy between the designation of the imaging direction and the arrangement state (the position and direction of the radiation generation unit 22 and the radiography unit 23) of the C-arm 25, that is, information indicating a direction and an amount in which the C-arm 25 is to be moved or rotated. The direction and the amount in which the C-arm 25 is to be moved or rotated can be calculated using two of the angle θ, the angle φ, and the distance "R", and the arrangement state of the C-arm 25.

Figure 14:
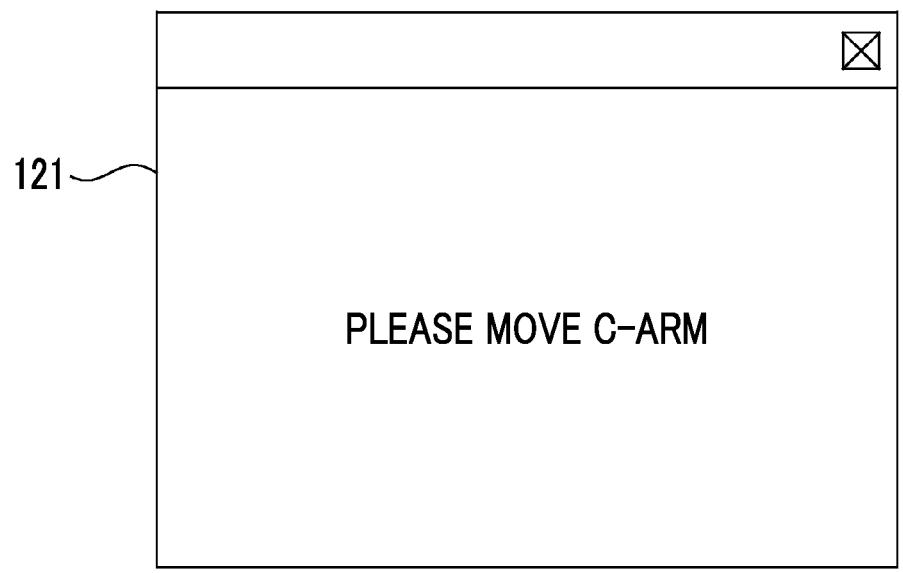
FIG. 14 is an example of a message for prompting movement of the C-arm.

As shown in FIG. 14, the notification unit 107 prompts the movement of the C-arm 25 by displaying a message 121, such as "Please move C-arm", for example, on at least one of the console, the first operating unit 71, the second operating unit 72, or the like. As the notification unit 107 prompts the movement of the C-arm 25, the operator can know, at an appropriate timing, that the movement of the C-arm 25 is needed in order to image the subject 15 from a desired imaging direction. For this reason, it is possible to allow the operator to efficiently carry out imaging. In a case where the message 121 is displayed on at least one of the first operating unit 71 or the second operating unit 72 (in particular, the validated first operating unit 71 or second operating unit 72), the operator can know that the movement of the C-arm 25 is needed while staying near the subject 15 or the C-arm 25 without moving to the console. As a result, it is possible to allow the operator to perform a movement operation of the C-arm 25 on the spot. Accordingly, it is possible to allow the operator to particularly efficiently carry out imaging.

The notification unit 107 can also give notification of at least one of the direction or the amount of movement of the C-arm 25 as a support member in the message 121. As at least one of the direction or the amount of movement of the C-arm 25 is indicated, it is possible to support the movement of the C-arm 25, or the like. For example, since the operator can know at least one of the direction or the amount in which the C-arm 25 is to be moved in order to image the subject 15 from a desired imaging direction, it is possible to allow the operator to efficiently move the C-arm 25 and to quickly carry out desired imaging. The direction of movement of the C-arm 25 is at least one of a direction in which the C-arm 25 is slid by the sliding mechanism 51 or a direction in which the C-arm 25 is rotated together with the sliding mechanism 51. The amount of movement of the C-arm 25 is at least one of a length (distance) at which the C-arm 25 is slid by the sliding mechanism 51 or an angle at which the C-arm 25 is rotated together with the sliding mechanism 51.

The notification unit 107 can give notification of information to the effect that the C-arm 25 is to be moved, at least one of the direction of movement of the C-arm 25 or the amount of movement of the C-arm 25, and the like in a form other than the message 121. For example, the notification unit 107 can give notification of information to the effect that the C-arm 25 is to be moved, at least one of the direction of movement of the C-arm 25 or the amount of movement of the C-arm 25, and the like by notifying the content of the message 121 by issuing beep, warning sound, voice, or other kinds of sound, turning on or off turning off an indicator (including an indicator displayed on a screen), such as a lamp, changing the color, brightness, or the like of the indicator, or using vibration or the like.

Figure 15:
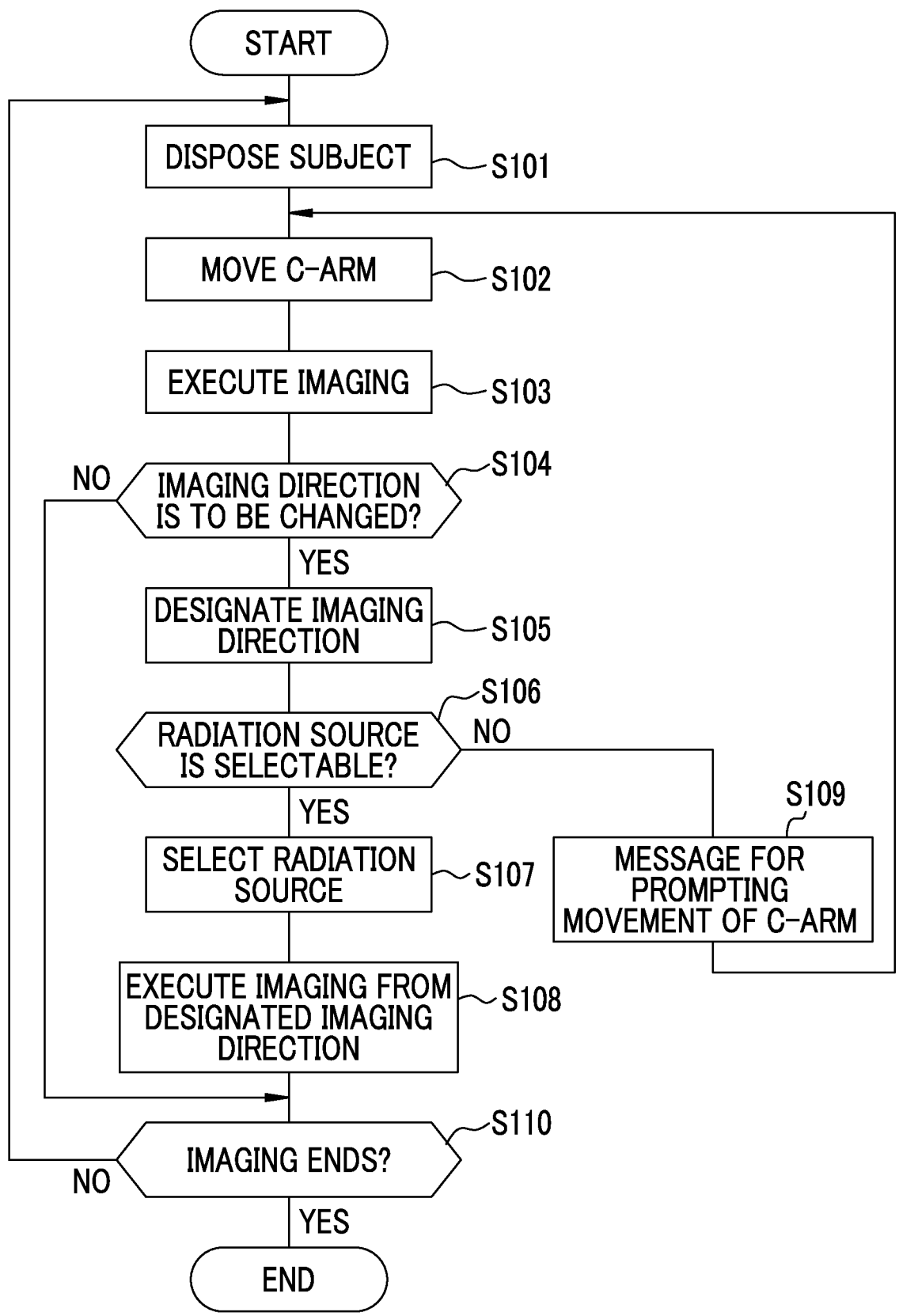
FIG. 15 is a flowchart showing the operation of the radiography apparatus.

Hereinafter, the operation of the radiography apparatus 10 configured as above will be described. As shown in FIG. 15, the operator first disposes the subject 15 on the bed 49 (Step S101). Next, as the C-arm 25 is moved (Step S102), the positions of the radiation generation unit 22 and the radiography unit 23 are aligned with respect to the subject 15. Then, as the operator sets the imaging form, such as fluoroscopy, and the imaging conditions, and then, inputs the imaging instruction to the radiography apparatus 10, the image acquisition unit 106 executes radiography according to the conditions (Step S103). Radiographic images and the like obtained by imaging is sequentially displayed on the monitor 37.

Thereafter, in a case where there is a need to change the imaging direction (Step S104), the radiography apparatus 10 receives an input of an imaging direction from the first operating unit 71 or the second operating unit 72 (Step S105). In a case where the imaging direction designation unit 101 designates the imaging direction based on the input, and in a case where one radiation source is selectable from among a plurality of radiation sources A11 to Aij using the designation of the imaging direction (Step S106: YES), the radiation source selection unit 102 selects one radiation source matching the designation of the imaging direction or one radiation source closest to the designation of the imaging direction (Step S107).

In a case where the radiation source selection unit 102 selects one radiation source using the designation of the imaging direction, the image acquisition unit 106 executes imaging using the selected radiation source. With this, the subject 15 is imaged from the imaging direction designated by the operator (Step S108).

In a case where the radiation source selection unit 102 cannot select one radiation source from among a plurality of radiation sources A11 to Aij using the designation of the imaging direction (Step S106: NO), the notification unit 107 prompts the movement of the C-arm 25 through the message 121 or the like (Step S109). For this reason, the operator adjusts the positions of the radiation generation unit 22 and the radiography unit 23 with respect to the subject 15 by moving the C-arm 25 according to the message 121 or the like (Step S102), and thereafter, executes imaging (Step S103). The operation of the radiography apparatus 10 described above is repeatedly performed until imaging ends (Step S110).

As described above, in a case where there is a need to change the imaging direction, the radiography apparatus 10 can designate an imaging direction and can automatically select a radiation source matching the designation of the imaging direction to carry out imaging. As a result, it is possible to allow the operator to efficiently perform imaging without needing to move or rotate the C-arm 25 each time there is change in imaging direction. In particular, in a case where the radiation generation unit 22 and the radiography unit 23 are supported by a support member, such as the C-arm 25, it is possible to simply image the subject 15 from a plurality of directions. For example, in a case where an artificial object, such as a bolt, is inserted into a human body as a subject, imaging is performed from a plurality of directions in conformity with the axis of the bolt or the like in order to confirm whether or not the bolt or the like is correctly inserted. In this case, in a case where imaging from a specific imaging direction is finished, there is a need to change the imaging direction; however, with the radiography apparatus 10, it is possible to image the subject 15 from another imaging direction only by inputting the imaging direction without moving or the like the C-arm 25.

In the first embodiment, although the first operating unit 71 is provided in the first end portion 41 of the C-arm 25, and the second operating unit 72 is provided in the second end portion 43 of the C-arm 25, the operating units may be provided at other arbitrary places. However, it is preferable that at least one of the first operating unit 71 or the second operating unit 72 may be provided in the radiation generation unit 22, the C-arm 25 as a support member, the radiography unit 23, or the like. This is because it is possible to allow the operator to efficiently carry out imaging as the operating units are provided within a range in which the operating units can be immediately operated, compared to a case where the operator returns to the console. In particular, it is preferable that the first operating unit 71 is provided in either of the radiation generation unit 22 or the first end portion 41 of the C-arm 25 as a support member. This is because the operator is likely to immediately perform the input of the imaging direction, and the like in a case where the operator holds or the like near the first end portion 41 to operate the C-arm 25. Similarly, it is preferable that the second operating unit 72 is provided in either of the radiography unit 23 or the second end portion 43 of the C-arm 25 as a support member. This is because the operator is likely to immediately perform the input of the imaging direction, and the like in a case where the operator holds or the like near the second end portion 43 to operate the C-arm 25.

In a case where the radiography apparatus 10 includes a terminal (for example, a tablet type terminal for an operation) for an operation in addition to the above-described configuration, the first operating unit 71 and the second operating unit 72 can be constituted using the terminal.

In the first embodiment, although the first operating unit 71 and the second operating unit 72 are provided, only either of the first operating unit 71 or the second operating unit 72 may be provided according to a use aspect or the like of the radiography apparatus 10. For example, between the first operating unit 71 and the second operating unit 72, one operating unit that is frequently used by the operator can be provided, and the other operating unit can be omitted. In a case where the first operating unit 71 is provided, it is possible to improve operability in an imaging form (so-called over-tube) in which the radiation generation unit 22 is on the vertical upward direction side with respect to the radiography unit 23. In a case where the second operating unit 72 is provided, it is possible to improve operability in an imaging form (so-called under-tube) in which the radiation generation unit 22 is on the vertical downward direction side with respect to the radiography unit 23.

In the first embodiment, although the first operating unit 71 and the second operating unit 72 receive the input of the imaging direction, the first operating unit 71 and the second operating unit 72 can indirectly receive the input of the imaging direction by receiving the selection of the radiation source for use in imaging among a plurality of radiation sources A11 to Aij. This is because the imaging direction and the selection of the radiation source for use in imaging have a given correspondence relationship (see FIG. 11). In a case where the first operating unit 71 and the second operating unit 72 receive the input of the imaging direction, there is an advantage that the operator is likely to intuitively operate the operating units. On the other hand, in a case where the first operating unit 71 and the second operating unit 72 receive the selection of the radiation source for use in imaging, there is an advantage that imaging can be carried out reliably using the radiation source designated by the operator. The first operating unit 71 and the second operating unit 72 suitably provide a user interface according to the content of the input. For example, in a case where the selection of the radiation source for use in imaging is received, an arrangement (see FIG. 6) of a plurality of radiation sources A11 to Aij is presented by a selectable screen display or an arrangement of pressable buttons and the like.

Second Embodiment

In the first embodiment, although radiographic images are not used in designating the imaging direction, the radiography apparatus 10 can designate the imaging direction using radiographic images. In the second embodiment, in particular, an example where the imaging direction is designated using radiographic images captured using at least two radiation sources, respectively, among a plurality of radiation sources A11 to Aij will be described.

Figure 16:
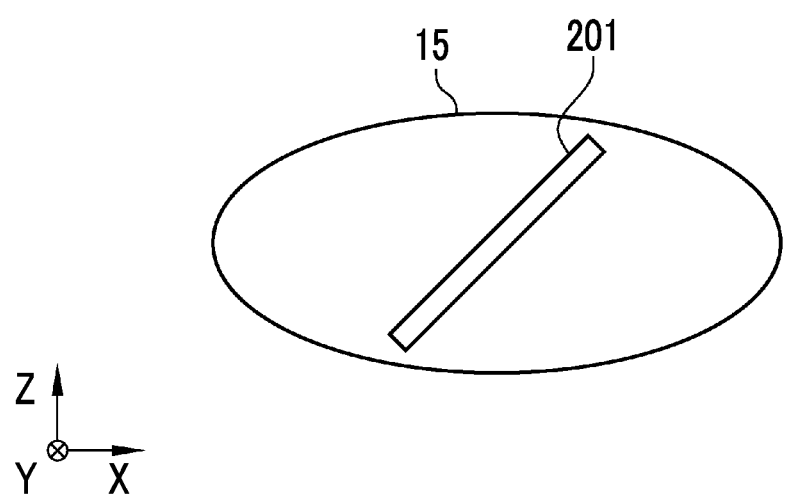
FIG. 16 is an explanatory view of a subject into which an artificial object is inserted.
Figure 17:
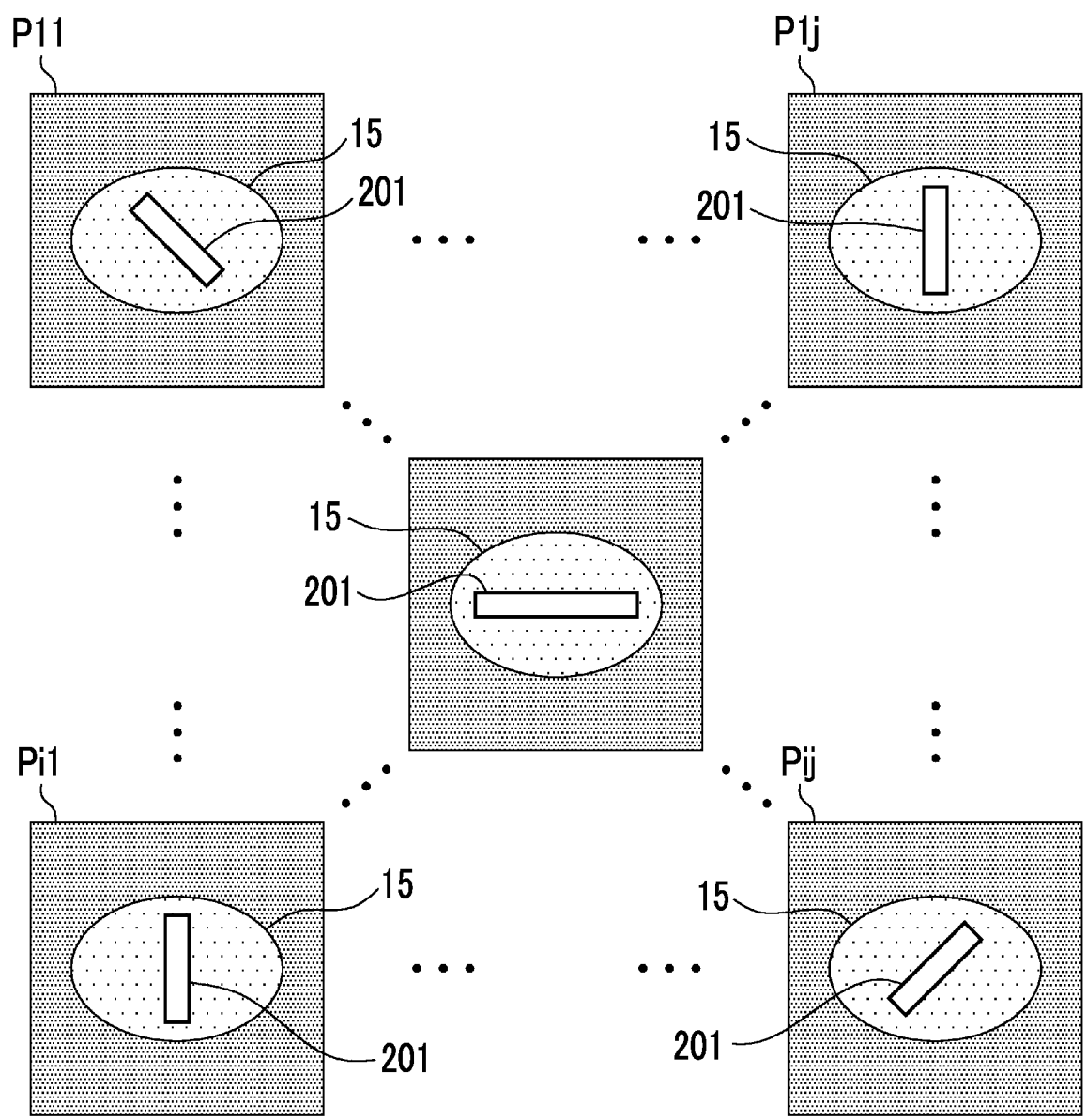
FIG. 17 is an example of radiographic images captured using a plurality of radiation sources.

As shown in FIG. 16, it is assumed that an artificial object 201, such as a bolt, is inserted into the subject 15. In this case, as shown in FIG. 17, in a plurality of radiographic images P11 to Pij obtained by imaging the subject 15 using a plurality of radiation sources A11 to Aij, respectively, are different in the size and shape of the subject 15, the position, size, and shape of the artificial object 201, and the like.

Figure 18:
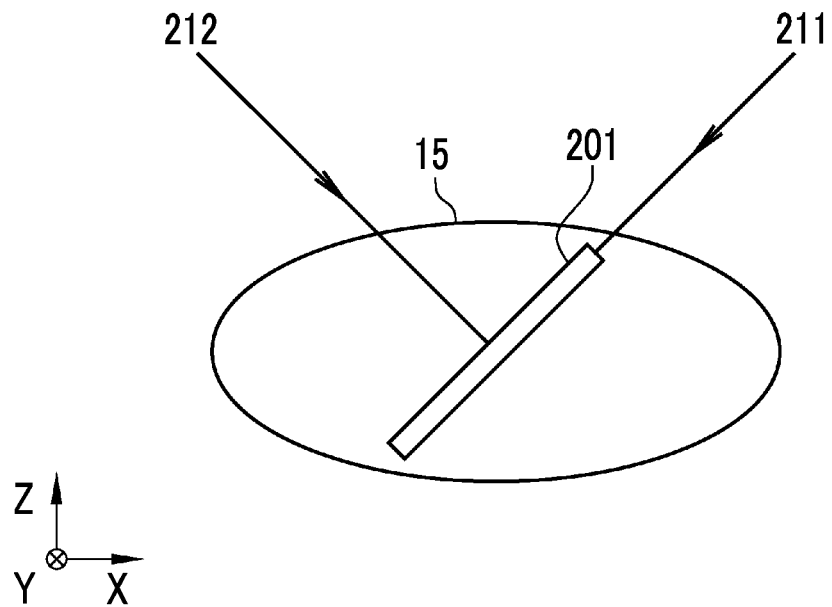
FIG. 18 is an explanatory view showing two kinds of imaging directions that can be designated.

In the embodiment, the imaging direction designation unit 101 automatically designates an imaging direction using at least two radiographic images among the radiographic images P11 to Pij, instead of using the input from the first operating unit 71 or the second operating unit 72 as in the first embodiment. As shown in FIG. 18, the imaging direction designated by the imaging direction designation unit 101 is a direction 211 substantially parallel to a longitudinal direction of the artificial object 201 or a direction 212 substantially perpendicular to the longitudinal direction of the artificial object 201. This is because, as described above, in a case where the artificial object 201 is inserted into the subject 15, normally, imaging from the direction substantially parallel to the longitudinal direction of the artificial object 201 and imaging from the direction substantially perpendicular to the longitudinal direction of the artificial object 201 are needed. The imaging direction designation unit 101 determines whether to designate the direction 211 substantially parallel to the longitudinal direction of the artificial object 201 or the direction 212 substantially perpendicular to the longitudinal direction of the artificial object 201 as the imaging direction according to setting or the like.

Hereinafter, for simplification, imaging direction designation unit 101 designates an imaging direction using the radiographic image P11 and the radiographic image Pij among the radiographic images P11 to Pij. In this case, the imaging direction designation unit 101 recognizes the artificial object 201 of each of the radiographic image P11 and the radiographic image Pij. On the other hand, the imaging direction of each of the radiographic image P11 and the radiographic image Pij with respect to the subject 15 is known at the time of the acquisition of the radiographic image P11 and the radiographic image Pij. For this reason, the imaging direction designation unit 101 can specify the direction 211 substantially parallel to the longitudinal direction of the artificial object 201 and can designate the direction 211 as the imaging direction using a position, a direction, and the like of the artificial object 201 in the radiographic image P11, a position, a direction, and the like of the artificial object 201 in the radiographic image Pij, and information regarding the imaging direction of each of the radiographic image P11 and the radiographic image Pij with respect to the subject 15. The direction 211 substantially parallel to the longitudinal direction of the artificial object 201 can be specified, as a result of which the imaging direction designation unit 101 can specify the direction 212 substantially perpendicular to the longitudinal direction of the artificial object 201 and can designate the direction 212 as the imaging direction. The operation of the radiography apparatus 10 after the imaging direction is designated is the same as in the first embodiment.

As described above, in a case where the imaging direction is designated using at least two radiographic images among the radiographic images P11 to Pij, it is possible to designate the imaging direction only by acquiring needed radiographic images among the radiographic images P11 to Pij even though there is no input using the first operating unit 71 or the second operating unit 72. For this reason, in a case where there is a need to change the imaging direction after a tomographic image is acquired, it is possible to particularly efficiently perform the designation of the imaging direction.

The imaging direction designation unit 101 can recognize the artificial object 201 using at least one of a contour shape, a pixel value (density), or the like. Alternatively, the imaging direction designation unit 101 may recognize the artificial object 201 using a so-called learned artificial intelligence (AI) program.

In the second embodiment, although the imaging direction designation unit 101 automatically designates the imaging direction using the radiographic images, in a case where a radiographic image is displayed on the display unit, it is possible to receive the input of the imaging direction in the radiographic image displayed on the display unit. For example, at least one radiographic image is displayed on at least one of the first operating unit 71 or the second operating unit 72. That is, at least one of the first operating unit 71 or the second operating unit 72 is a display unit that displays a radiographic image. Then, at least one of the first operating unit 71 or the second operating unit 72 receives an input of an imaging direction in the displayed radiographic image.

Figure 19:
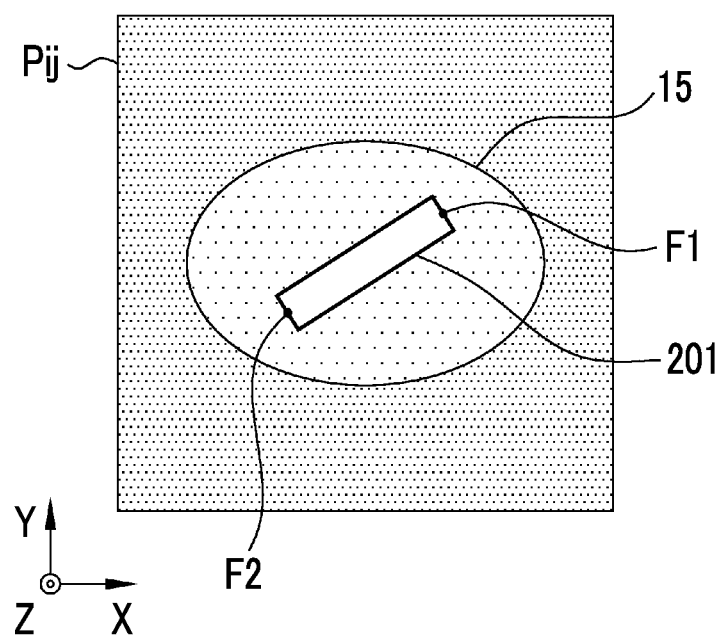
FIG. 19 is an example of two points to be selected.

The input of the imaging direction in the radiographic image is performed by receiving selection of two or more points in the radiographic image. The "selection of two or more points" includes an input of a line segment, a straight line, or a half-line representing the imaging direction. This is because the selection of two or more points and an input of a straight line or the like passing through the two or more points have the same meaning in designating the imaging direction. "Passing" through two or more points refers to passing substantially near the two or more points, and the straight line or the like passing through the two or more points includes a straight line or the like (so-called regression straight line) by a least square method or other kinds of analysis. In the modification example, as shown in FIG. 19, the operator recognizes the artificial object 201 by viewing one tomographic image Pij displayed on the first operating unit 71 or the like and selects two points F1 and F2 along a direction to set as an imaging direction, such as both ends.

Then, the imaging direction designation unit 101 designates an imaging direction based on positions of the selected two points F1 and F2. Specifically, the imaging direction designation unit 101 designates an imaging direction parallel to or perpendicular to a three-dimensional straight line passing through the selected two points F1 and F2. For example, the imaging direction designation unit 101 can specify a three-dimensional direction (a stereoscopic direction in a real space, not on an image) of the straight line passing through the points F1 and F2 using the input positions (coordinates) of the points F1 and F2, the position of the artificial object 201 in other radiographic images, and the like. As a result, the imaging direction designation unit 101 designates a direction substantially parallel to the three-dimensional straight line passing through the points F1 and F2 or a direction substantially perpendicular to the three-dimensional straight line passing through the points F1 and F2 as the imaging direction.

In this way, in a case where the selection of the two or more points in the displayed radiographic image is received, and the imaging direction designation unit 101 designates the imaging direction based on the positions of the selected two or more points, the imaging direction designation unit 101 can designate the imaging direction according to the recognition and intention of the operator.

In a case where two or more radiographic images P11 to Pij (for examples, the radiographic image P11 and the radiographic image Pij) are displayed on the first operating unit 71 or the like, not only selection of two or more points in one radiographic image among the radiographic images can be received, but also selection of two or more points by dispersing one point in each of two tomographic images can be received.

In the modification example, although the selection of the two or more points in the radiographic images P11 to Pij is received for the designation of the imaging direction, instead, as selection of a structure included in the subject 15 in the radiographic images P11 to Pij is received, the imaging direction designation unit 101 can designate an imaging direction based on a position, a shape, or the like of the selected structure. For example, in a case where a portion in which the artificial object 201 as a structure is present in the displayed radiographic image P11 or the like is selected using the first operating unit 71 or the like, the imaging direction designation unit 101 can specify the longitudinal direction of the selected artificial object 201 as a structure or a direction perpendicular to the longitudinal direction. As a result, the imaging direction designation unit 101 can designate a direction substantially parallel to the longitudinal direction of the artificial object 201 as a structure or a direction substantially perpendicular to the longitudinal direction of the artificial object 201 as a structure as an imaging direction. In this way, as the selection of the structure is received using the radiographic image, in a case where the imaging direction designation unit 101 designates an imaging direction, the structure to be considered by the imaging direction designation unit 101 for the designation of the imaging direction becomes clear. As a result, it is possible to accurately designate the imaging direction. For example, it is particularly useful in a case where there are two or more artificial object 201 in the subject 15, a case where one artificial object 201 is composed of two or more parts, or the like.

In the second embodiment and the modification example, although the imaging direction is designated using the radiographic image displayed on the first operating unit 71 or the like, in a case where the tomographic image acquisition unit 118 acquires a tomographic image, an input of setting or change of parameters for forming a tomographic image in the radiographic image displayed on the first operating unit 71 or the like can be received.

For example, the tomographic image acquisition unit 118 can receive at least one of selection of a slice direction or selection of a slice position in the radiographic image displayed on the first operating unit 71 or the like. The slice direction is a direction in which a tomographic image is formed with respect to the subject 15, that is, a direction of a cross section. The slice position is a position where a tomographic image is formed with respect to the subject 15, that is, a depth of a specific cross section at which a tomographic image is generated.

In selecting at least one of the slice direction or the slice position, the tomographic image acquisition unit 118 can use positions of two points F1 and F2 (in a case where two or more points are selected, the two or more points) for the input of the imaging direction. That is, in a case where the selection of the two points F1 and F2 in the radiographic image Pij displayed on the first operating unit 71 or the like is received (see FIG. 19), the tomographic image acquisition unit 118 changes at least one of the slice direction or the slice position based on the selected two points F1 and F2, and the imaging direction designation unit 101 designates the imaging direction based on the positions of the selected two points F1 and F2. In this case, the tomographic image acquisition unit 118 can specify the direction of the artificial object 201 by acquiring information from the imaging direction designation unit 101 or in the same manner as the method that is performed by the imaging direction designation unit 101.

Figure 20:
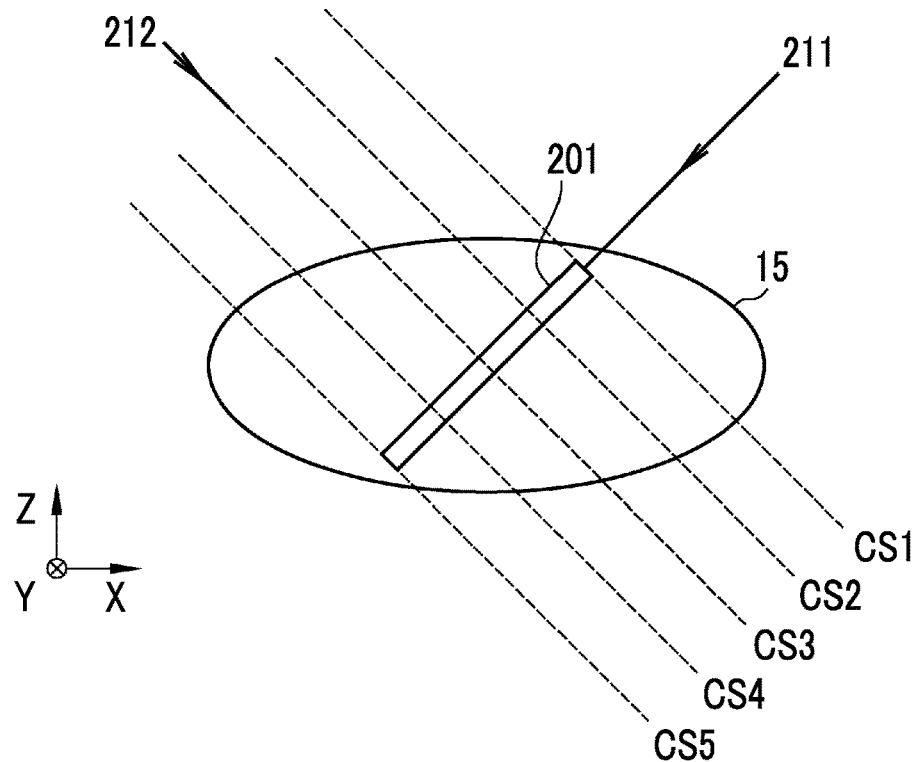
FIG. 20 is an example of a slice direction after change.
Figure 21:
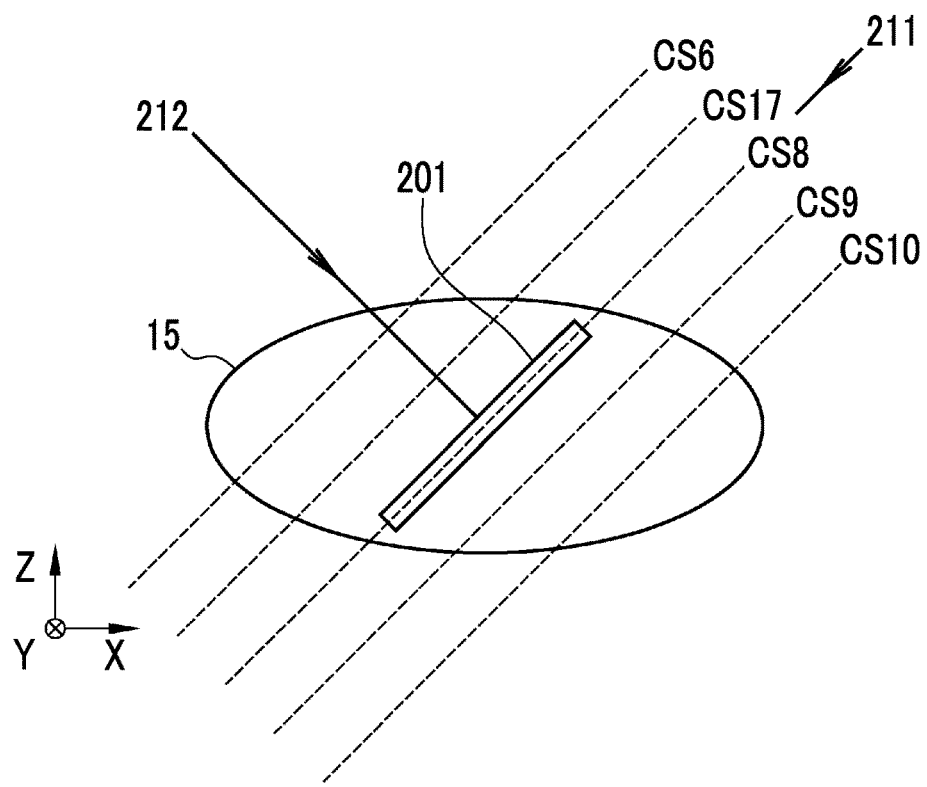
FIG. 21 is an example of a slice direction after change.

As a result, the tomographic image acquisition unit 118 can automatically set or change the slice direction to a direction substantially perpendicular to the longitudinal direction of the artificial object 201 like cross sections CS1 to CS5 shown in FIG. 20. Furthermore, the tomographic image acquisition unit 118 can automatically set or change the slice direction to a direction parallel to the longitudinal direction of the artificial object 201 like cross sections CS6 to CS10 shown in FIG. 21. In a case where the artificial object 201 is inserted into the subject 15, a tomographic image in a slice direction parallel to or perpendicular to the longitudinal direction of the artificial object 201 is useful in confirming whether or not the artificial object 201 is correctly inserted, or the like. For this reason, in a case where the slice direction is automatically set in the above-described manner, it is possible to efficiently obtain tomographic images in the slice directions.

Since the tomographic image acquisition unit 118 can specify the direction of the artificial object 201, the tomographic image acquisition unit 118 can automatically set or change the slice position of the tomographic image for use in display or the like. For example, the tomographic image acquisition unit 118 can automatically select a tomographic image or the like related to a cross section (for example, the cross section CS8 of FIG. 21) passing through the artificial object 201 or a cross section (for example, the cross section CS3 of FIG. 20) passing through the center of the artificial object 201 based on setting or the like and can display or the like the tomographic image. In a case where the slice position is automatically set or changed, there is an advantage that a tomographic image or tomographic video desired by the operator is likely to be provided in a case where a specific tomographic image out of a series of tomographic images is displayed and in a case where tomographic video related to a specific cross section is displayed. In particular, in a case where the slice direction is changed, the slice position of the tomographic image for use in display or the like is further automatically adjusted in the above-described manner, whereby a tomographic image desired by the operator is likely to be provided even after the slice direction is changed.

Two points for selecting at least one of the slice direction or the slice position may be input separately from the two points F1 and F2 for designating the imaging direction. Two points for selecting the slice direction and Two points for selecting the slice position may be input individually. However, in a case where the two points F1 and F2 for designating the imaging direction and the two points for selecting at least one of the slice direction or the slice position are common, since the selection of the imaging direction and at least one of the slice direction or the slice position is completed only with single (a set of the points F1 and F2) selection, it is possible to particularly efficiently carry out imaging. The same applies to a case where two or more points for designating the imaging direction and at least one of two or more points for selecting the slice direction or the points for selecting the slice position are selected. A part or all of the points for designating the imaging direction and at least one of the points for selecting the slice direction or the points for selecting the slice position are made common, whereby it is possible to efficiently carry out imaging.

The same applies to a case where the selection of the structure is received. That is, in selecting at least one of the slice direction or the slice position, the tomographic image acquisition unit 118 can use the position or the shape of the structure selected for the input of the imaging direction. Specifically, in a case where the selection of the structure included in the subject 15 in the radiographic image displayed on the first operating unit 71 or the like is received, the tomographic image acquisition unit 118 changes at least one of the slice direction or the slice position based on the position or the shape of the selected structure, and the imaging direction designation unit 101 can designate the imaging direction based on the position or the shape of the selected structure. In this case, the tomographic image acquisition unit 118 can specify the position or the shape of the selected structure by acquiring information from the imaging direction designation unit 101 or in the same manner as the method performed by the imaging direction designation unit 101. Accordingly, the tomographic image acquisition unit 118 can change the slice direction to, for example, a direction substantially parallel to a longitudinal direction of the selected structure or a direction substantially perpendicular to the longitudinal direction of the selected structure and can efficiently obtain tomographic images in the slice directions. Since the tomographic image acquisition unit 118 can specify the position, the shape, or the like of the selected structure, the tomographic image acquisition unit 118 can also automatically set or change the slice position of the tomographic image for use in display or the like based on the position, the shape, or the like of the selected structure. In a case where the slice position is automatically set or changed, there is an advantage that a tomographic image or tomographic video desired by the operator is likely to be provided. In particular, in a case where the slice direction is changed, the slice position of the tomographic image for use in display or the like is further automatically adjusted, whereby a tomographic image desired by the operator is likely to be provided even after the slice direction is changed.

In the first embodiment, the second embodiment, and the modification examples, in a case where fluoroscopy is performed on the subject 15, it is preferable that the tomographic image acquisition unit 118 automatically acquires a tomographic image through imaging after fluoroscopy ends. Normally, in a case where fluoroscopy is finished, a fluoroscopic image of the last frame of fluoroscopy is continuously displayed on the monitor 37 or the like. Then, the operator inputs or the like the next imaging direction while imaging a three-dimensional structure of the subject 15 based on the fluoroscopic image of the last frame. For this reason, the setting of the next imaging direction, and the like vary depending on the skill of the operator. Accordingly, in the radiography apparatus 10, the tomographic image acquisition unit 118 automatically acquires a tomographic image after fluoroscopy ends. As a result, the operator can accurately ascertain the three-dimensional structure of the subject 15 while viewing the tomographic image after fluoroscopy ends without depending on the skill, and can accurately perform the input of the imaging direction, and the like.

As described in the respective embodiments and the like, as one form of the invention, there is provided an operation method for a radiography apparatus having a radiation generation unit that has a plurality of radiation sources generating radiation toward a subject, a support member that supports the radiation generation unit in a first end portion as one end of the support member, and a radiography unit that is provided in a second end portion as the other end of the support member to face the radiation generation unit and images the subject using radiation. The operation method for the radiography apparatus comprises a step in which the imaging direction designation unit designates an imaging direction of the subject, and a step in which the radiation source selection unit selects the radiation source for use in imaging among a plurality of radiation sources using the designation of the imaging direction. The operation method is one form of the invention. Furthermore, as one form of the invention, there is also provided an operation program for a radiography apparatus having a radiation generation unit that has a plurality of radiation sources generating radiation toward a subject, a support member that supports the radiation generation unit in a first end portion as one end of the support member, and a radiography unit that is provided in a second end portion as the other end of the support member to face the radiation generation unit and images the subject using radiation. The operation program causes the imaging unit body 21, the console, or the like to execute a step in which the imaging direction designation unit designates an imaging direction of the subject, and a step in which the radiation source selection unit selects the radiation source for use in imaging among a plurality of radiation sources using the designation of the imaging direction.

In the respective embodiments and the like, although the support member that supports the radiation generation unit 22 and the radiography unit 23 is the C-arm 25, a form of the support member is arbitrary. In the respective embodiments and the like, although the radiography apparatus 10 having the C-arm 25 has been specifically described as an example, the invention is suitable for a radiography apparatus in arbitrary form in which the radiation generation unit 22 and the radiography unit 23 are supported by a support member (including a case where the support member is composed of one or a plurality of members), thereby regulating the positional relationship between the radiation generation unit 22 and the radiography unit 23.

The configurations of the respective embodiments and the like can be arbitrarily combined and used. The configurations of the respective embodiments and the like can be partially combined with other embodiments and the like and used.

In the respective embodiments and the like, although the image acquisition unit 106 and the general image acquisition unit 116, the fluoroscopic image acquisition unit 117, and the tomographic image acquisition unit 118 constituting the image acquisition unit 106 acquire radiographic images through imaging, the image acquisition unit 106 and the like can acquire previously captured radiographic images from a device, a system, or the like connected to the radiography apparatus 10, such as a radiology information system (RIS) and can use the radiographic images for display.

In the respective embodiments and the like, although the imaging direction designation unit 101, the radiation source selection unit 102, the imaging condition designation unit 103, the controller 104, the image acquisition unit 106, the operation setting unit 111, the general image acquisition unit 116, the fluoroscopic image acquisition unit 117, the tomographic image acquisition unit 118, the notification unit 107, and the like are provided in the imaging unit body 21, a part or all of the configurations can be provided in a console, the display unit body 36, another processing device (including a device connected through a network) connected to the radiography apparatus 10, or the like.

In the respective embodiments and the like, the hardware structures of the processing units that execute various kinds of processing, such as the imaging direction designation unit 101, the radiation source selection unit 102, the imaging condition designation unit 103, the controller 104, the image acquisition unit 106, the operation setting unit 111, the general image acquisition unit 116, the fluoroscopic image acquisition unit 117, the tomographic image acquisition unit 118, and the notification unit 107, are various processors described below. Various processors include a central processing unit (CPU) or a graphic processing unit (GPU) that is a general-purpose processor executing software (program) to function as various processing units, a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like.

One processing unit may be configured of one of various processors described above or may be configured of a combination of two or more processors (for example, a plurality of FPGAs, a combination of a CPU and an FPGA, a combination of a CPU and a GPU, or the like) of the same type or different types. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

EXPLANATION OF REFERENCES

10: radiography apparatus
11: imaging unit
12: display unit
15: subject
21: imaging unit body
22: radiation generation unit
23: radiography unit
25: C-arm
27: caster
31: cable
36: display unit body
37: monitor
41: first end portion
42: arrow
43: second end portion
44: detection unit
46: arrow
47: center line
49: bed
51: sliding mechanism
52: lifting mechanism
61: drive circuit
62: collimator
63: irradiation range display unit
71: first operating unit
72: second operating unit
81: imaging direction input unit
82: imaging condition input unit
83: imaging direction input unit
84: imaging condition input unit
86: radiography panel
87: grid
88: battery
101: imaging direction designation unit
102: radiation source selection unit
103: imaging condition designation unit
104: controller
106: image acquisition unit
107: notification unit
111: operation setting unit
116: general image acquisition unit
117: fluoroscopic image acquisition unit
118: tomographic image acquisition unit
121: message
201: artificial object
211: direction substantially parallel to longitudinal direction of artificial object
212: direction substantially perpendicular to longitudinal direction of artificial object
A11 to Aij: radiation source
Amn: radiation source
C1: center
C2: center
CS1 to CS10: cross section
Dmn: imaging direction
E1: axis
F1: point
F2: point
P11 to Pij: radiographic image
S101 to S110: step

What is claimed is:

1. A radiography apparatus comprising:
a radiation generation unit that has a plurality of radiation sources generating radiation toward a subject;
a support member that supports the radiation generation unit in a first end portion as one end of the support member;
a radiography unit that is provided to face the radiation generation unit in a second end portion as the other end of the support member and images the subject using the radiation; and
a processor configured to function as:
an imaging direction designation unit that designates an imaging direction of the subject; and
a radiation source selection unit that selects the radiation source for use in imaging among the plurality of the radiation sources using the designation of the imaging direction,
wherein the imaging direction designation unit designates the imaging direction based on an input from an operating unit provided in the radiation generation unit, the support member, or the radiography unit.

2. The radiography apparatus according to claim 1,
wherein the operating unit is provided in the radiation generation unit or the first end portion of the support member.

3. The radiography apparatus according to claim 1,
wherein the operating unit is provided in the radiography unit or the second end portion of the support member.

4. The radiography apparatus according to claim 1,
wherein the imaging direction designation unit is connected to a first operating unit provided in the radiation generation unit or the first end portion of the support member and a second operating unit provided in the radiography unit or the second end portion of the support member, and
the first operating unit is validated in a case where the radiation generation unit is on a vertical upward direction side with respect to the radiography unit, and the second operating unit is validated in a case where the radiation generation unit is on a vertical downward direction side with respect to the radiography unit.

5. The radiography apparatus according to claim 1,
wherein the operating unit displays the imaging direction.

6. The radiography apparatus according to claim 1,
wherein the operating unit receives an input of the imaging direction.

7. The radiography apparatus according to claim 6,
wherein the operating unit receives the input of the imaging direction indirectly by receiving the selection of the radiation source for use in imaging among the plurality of radiation sources.

8. The radiography apparatus according to claim 6,
wherein the operating unit receives the input of the imaging direction through a touch of an operator.

9. The radiography apparatus according to claim 6,
wherein the operating unit receives the input of the imaging direction through motion or voice of an operator.

10. A radiography apparatus comprising:
a radiation generation unit that has a plurality of radiation sources generating radiation toward a subject;

a support member that supports the radiation generation unit in a first end portion as one end of the support member;

a radiography unit that is provided to face the radiation generation unit in a second end portion as the other end of the support member and images the subject using the radiation; and a processor configured to function as:

an imaging direction designation unit that designates an imaging direction of the subject; and a radiation source selection unit that selects the radiation source for use in imaging among the plurality of the radiation sources using the designation of the imaging direction, wherein the processor further configured to function as:

a notification unit that prompts movement of the support member in a case where the radiation source selection unit is unable to select the radiation source using the imaging direction designated by the imaging direction designation unit.

11. The radiography apparatus according to claim 10, wherein the imaging direction designation unit designates the imaging direction using a radiographic image.

12. The radiography apparatus according to claim 11, further comprising:

a display unit that displays the radiographic image, wherein an input of the imaging direction is received in the radiographic image displayed on the display unit.

13. The radiography apparatus according to claim 12, wherein selection of two or more points in the radiographic image is received, and the imaging direction designation unit designates the imaging direction based on positions of the selected two or more points.

14. The radiography apparatus according to claim 13, wherein the imaging direction designation unit designates the imaging direction parallel to or perpendicular to a three-dimensional straight line passing through the selected two or more points.

15. The radiography apparatus according to claim 12, wherein selection of a structure included in the subject in the radiographic image is received, and the imaging direction designation unit designates the imaging direction based on a position or a shape of the selected structure.

16. The radiography apparatus according to claim 15, wherein the imaging direction designation unit designates a direction parallel to a longitudinal direction of the structure or a direction perpendicular to the longitudinal direction of the structure as the imaging direction.

17. The radiography apparatus according to claim 12, wherein, in a case where a tomographic image is acquired, at least one of selection of a slice direction as a direction of forming the tomographic image with respect to the subject in the radiographic image or selection of a slice position as a position for forming the tomographic image with respect to the subject in the radiographic image is received.

18. The radiography apparatus according to claim 17, wherein selection of two or more points in the radiographic image is received, at least one of the slice direction or the slice position is changed based on positions of the selected two or more points, and the imaging direction designation unit designates the imaging direction based on the positions of the selected two or more points.

19. The radiography apparatus according to claim 18, wherein selection of a structure included in the subject in the radiographic image is received, at least one of the slice direction or the slice position is changed based on a position or a shape of the selected structure, and the imaging direction designation unit designates the imaging direction based on the position or the shape of the selected structure.

20. The radiography apparatus according to claim 17, wherein tomographic video composed of the tomographic image is acquired by continuously or intermittently acquiring the tomographic image by imaging the subject.

21. The radiography apparatus according to claim 17, wherein, in a case where fluoroscopy is performed on the subject, the tomographic image is automatically acquired through imaging after fluoroscopy ends.

22. The radiography apparatus according to claim 10, wherein the notification unit gives notification of at least one of a direction of movement or an amount of movement of the support member.

* * * * *